(12) United States Patent
Myung et al.

(10) Patent No.: US 11,384,338 B2
(45) Date of Patent: Jul. 12, 2022

(54) ONCOLYTIC T7 BACTERIOPHAGE HAVING CYTOKINE GENE AND DISPLAYING HOMING PEPTIDE ON CAPSID AND ITS USE FOR TREATING MELANOMA

(71) Applicant: ARKGEN BIOSCIONS CO., LTD., Daejeon (KR)

(72) Inventors: Heejoon Myung, Yongin-si (KR); Yoonjung Hwang, Seongnam-si (KR)

(73) Assignee: ARKGEN BIOSCIONS CO., LTD, Daejeon (KR)

( * ) Notice: Subject to any disclaimer, the term of this patent is extended or adjusted under 35 U.S.C. 154(b) by 109 days.

(21) Appl. No.: 16/685,516

(22) Filed: Nov. 15, 2019

(65) Prior Publication Data
US 2021/0009963 A1    Jan. 14, 2021

(30) Foreign Application Priority Data

Jul. 8, 2019    (KR) ........................ 10-2019-0081977

(51) Int. Cl.
| | | |
|---|---|---|
| *C12N 7/00* | (2006.01) | |
| *A61P 35/00* | (2006.01) | |
| *A61K 35/768* | (2015.01) | |
| *C07K 14/535* | (2006.01) | |

(52) U.S. Cl.
CPC .............. *C12N 7/00* (2013.01); *A61K 35/768* (2013.01); *A61P 35/00* (2018.01); *C07K 14/535* (2013.01); *C12N 2795/10222* (2013.01); *C12N 2795/10232* (2013.01); *C12N 2795/10243* (2013.01); *C12N 2795/10271* (2013.01)

(58) Field of Classification Search
None
See application file for complete search history.

(56) References Cited

PUBLICATIONS

Dabrowska et al., "Antitumor Activity of Bacteriophages in Murine Experimental Cancer Models Caused Possibly by Inhibition of beta3 Integrin Signaling Pathway", Acta virologica. vol. 48, pp. 241-248, (2004).
Eriksson et al., "Tumor specific phage particles promote tumor regression in a mouse melanoma model", Cancer Immunol Immunother, vol. 56, pp. 677-687, (2007).
Puzanov et al., "Talimogene Laherparepvec in Combination With Ipilimumab in Previously Untreated, Unresectable Stage IIIB-IV Melanoma", Journal of Clinical Oncology, vol. 34, No. 22, p. 2619 (1-13), (2016).
Reale et al., "Perspectives on immunotherapy via oncolytic viruses", Infectious Agents and Cancer, vol. 14, No. 5, pp. 1-8, (2019).
Robilotti et al., "Viral oncolytic immunotherapy in the war on cancer: Infection control considerations", Infection Control & Hospital Epidemiology, vol. 40, pp. 350-354, (2019).

*Primary Examiner* — Nicole Kinsey White
(74) *Attorney, Agent, or Firm* — Vorys, Sater, Seymour & Pease LLP; Mih Suhn Koh

(57) ABSTRACT

Provided is an oncolytic recombinant bacteriophage T7 expressing a cytokine in eukaryotic cells and displaying on its capsid a tumor specific homing peptide, thus inducing direct lysis of target tumor cells and immunological response to the phage leading to the effective anticancer effect. The phage naturally infecting bacteria, not human beings, provides a great advantage for gene manipulation and production for the development of anticancer agents.

3 Claims, 7 Drawing Sheets
Specification includes a Sequence Listing.

(A)

(B)

SEQUENCE LISTING

<160> NUMBER OF SEQ ID NOS: 10

<210> SEQ ID NO 1
<211> LENGTH: 13
<212> TYPE: PRT
<213> ORGANISM: Artificial Sequence
<220> FEATURE:

-continued

```
<223> OTHER INFORMATION: Homing peptide

<400> SEQUENCE: 1

Cys Thr Val Ala Leu Pro Gly Gly Tyr Val Arg Val Cys
1               5                   10

<210> SEQ ID NO 2
<211> LENGTH: 5
<212> TYPE: PRT
<213> ORGANISM: Artificial Sequence
<220> FEATURE:
<223> OTHER INFORMATION: Homing peptide
<220> FEATURE:
<221> NAME/KEY: MOD_RES
<222> LOCATION: (4)
<223> OTHER INFORMATION: D-Form
<220> FEATURE:
<221> NAME/KEY: MOD_RES
<222> LOCATION: (5)
<223> OTHER INFORMATION: N-Methylvaline

<400> SEQUENCE: 2

Arg Gly Asp Phe Val
1               5

<210> SEQ ID NO 3
<211> LENGTH: 7
<212> TYPE: PRT
<213> ORGANISM: Artificial Sequence
<220> FEATURE:
<223> OTHER INFORMATION: Homing peptide
<220> FEATURE:
<221> NAME/KEY: MISC_FEATURE
<222> LOCATION: (5)..(6)
<223> OTHER INFORMATION: Any amino acids

<400> SEQUENCE: 3

Arg Thr Asp Leu Xaa Xaa Leu
1               5

<210> SEQ ID NO 4
<211> LENGTH: 12
<212> TYPE: PRT
<213> ORGANISM: Artificial Sequence
<220> FEATURE:
<223> OTHER INFORMATION: Homing peptide

<400> SEQUENCE: 4

Trp Gln Pro Asp Thr Ala His His Trp Ala Thr Leu
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Homing peptide

<400> SEQUENCE: 5

His Ala Ile Tyr Pro Arg His
1               5

<210> SEQ ID NO 6
<211> LENGTH: 12
<212> TYPE: PRT
<213> ORGANISM: Artificial Sequence
<220> FEATURE:
<223> OTHER INFORMATION: Homing peptide
```

<400> SEQUENCE: 6

Tyr Ser Ala Tyr Pro Asp Ser Val Pro Met Met Ser
1               5                   10

<210> SEQ ID NO 7
<211> LENGTH: 10
<212> TYPE: DNA
<213> ORGANISM: Artificial Sequence
<220> FEATURE:
<223> OTHER INFORMATION: KOZAK sequence
<220> FEATURE:
<221> NAME/KEY: misc_feature
<222> LOCATION: (4)
<223> OTHER INFORMATION: R: purine; A or G

<400> SEQUENCE: 7 gccrccatgg                                                              10

<210> SEQ ID NO 8
<211> LENGTH: 20
<212> TYPE: DNA
<213> ORGANISM: Artificial Sequence
<220> FEATURE:
<223> OTHER INFORMATION: Forward Primer

<400> SEQUENCE: 8
ggccttggaa gcatgtagag                                                   20

<210> SEQ ID NO 9
<211> LENGTH: 20
<212> TYPE: DNA
<213> ORGANISM: Artificial Sequence
<220> FEATURE:
<223> OTHER INFORMATION: Reverse Primer

<400> SEQUENCE: 9
ccgtagaccc tgctcgaata                                                   20

<210> SEQ ID NO 10
<211> LENGTH: 39937
<212> TYPE: DNA
<213> ORGANISM: Bacteriophage T7
<220> FEATURE:
<221> NAME/KEY: misc_feature
<222> LOCATION: (27223)..(27230)
<223> OTHER INFORMATION: PacI site

<400> SEQUENCE: 10
tctcacagtg tacggaccta aagttccccc atagggggta cctaaagccc agccaatcac        60
ctaaagtcaa ccttcggttg accttgaggg ttccctaagg gttggggatg acccttgggt       120
ttgtctttgg gtgttacctt gagtgtctct ctgtgtccct atctgttaca gtctcctaaa       180
gtatcctcct aaagtcacct cctaacgtcc atcctaaagc caacacctaa agcctacacc       240
taaagaccca tcaagtcaac gcctatctta aagtttaaac ataaagacca gacctaaaga       300
ccagacctaa agacactaca taaagaccag acctaaagac gccttgttgt tagccataaa       360
gtgataacct ttaatcattg tctttattaa tacaactcac tataaggaga gacaacttaa       420
agagacttaa aagattaatt taaaatttat caaaagagt attgacttaa agtctaacct        480
ataggatact tacagccatc gagagggaca cggcgaatag ccatcccaat cgacaccggg       540
gtcaaccgga taagtagaca gcctgataag tcgcacgaaa acaggtatt gacaacatga        600 agtaacatgc agtaagatac aaatcgctag gtaaacactag cagcgtcaac cgggcgcaca       660

```
gtgccttcta ggtgacttaa gcgcaccacg gcacataagg tgaaacaaaa cggttgacaa    720
catgaagtaa acacggtacg atgtaccaca tgaaacgaca gtgagtcacc acactgaaag    780
gtgatgcggt ctaacgaaac ctgacctaag acgctcttta acaatctggt aaatagctct    840
tgagtgcatg actagcggat aactcaaggg tatcgcaagg tgcccttttat gatattcact   900 aataactgca cgaggtaaca caagatggct atgtctaaca tgacttacaa caacgttttc    960
gaccacgctt acgaaatgct gaaagaaaac atccgttatg atgacatccg tgacactgat   1020
gacctgcacg atgctattca catggctgcc gataatgcag ttccgcacta ctacgctgac   1080
atctttagcg taatggcaag tgagggcatt gaccttgagt tcgaagactc tggtctgatg   1140
cctgacacca aggacgtaat ccgcatcctg caagcgcgta tctatgagca attaacgatt   1200
gacctctggg aagacgcaga agacttgctc aatgaatact tggaggaagt cgaggagtac   1260
gaggaggatg aagagtaatg tctactacca acgtgcaata cggtctgacc gctcaaactg   1320
tacttttcta tagcgacatg gtgcgctgtg gctttaactg gtcactcgca atggcacagc   1380
tcaaagaact gtacgaaaac aacaaggcaa tagctttaga atctgctgag tgatagactc   1440
aaggtcgctc ctagcgagtg gcctttatga ttatcacttt acttatgagg gagtaatgta   1500
tatgcttact atcggtctac tcaccgctct aggtctagct gtaggtgcat cctttgggaa   1560
ggctttaggt gtagctgtag gttcctactt taccgcttgc atcatcatag gaatcatcaa   1620
aggggcacta cgcaaatgat gaagcactac gttatgccaa tccacacgtc aacggggca    1680 accgtatgta cacctgatgg gttcgcaatg aaacaacgaa tcgaacgcct taagcgtgaa   1740
ctccgcatta accgcaagat taacaagata ggttccggct atgacagaac gcactgatgg   1800
cttaaagaaa ggttatatgc ccaatggcac actatacgct gcaaatcggc gaatagtgag   1860
aacttggcga gagaacaacc tcgaacgccg caaggacaag agagggcggc gtggcataga   1920
cgaaaggaaa aggttaaagc caagaaactc gccgcacttg aacaggcact agccaacaca   1980
ctgaacgcta tctcataacg aacataaagg acacaatgca atgaacatta ccgacatcat   2040
gaacgctatc gacgcaatca agcactgcc aatctgtgaa cttgacaagc gtcaaggtat   2100
gcttatcgac ttactggtcg agatggtcaa cagcgagacg tgtgatggcg agctaaccga   2160
actaaatcag gcacttgagc atcaagattg gtggactacc ttgaagtgtc tcacggctga   2220
cgcagggttc aagatgctcg gtaatggtca cttctcggct gcttatagtc acccgctgct   2280
acctaacaga gtgattaagg tgggctttaa gaaagaggat tcaggcgcag cctataccgc   2340
attctgccgc atgtatcagg tcgtcctgg tatccctaac gtctacgatg tacagcgcca    2400
cgctggatgc tatacggtgg tacttgacgc acttaaggat tgcgagcgtt tcaacaatga   2460
tgcccattat aaatacgctg agattgcaag cgacatcatt gattgcaatt cggatgagca   2520
tgatgagtta actggatggg atggtgagtt tgttgaaact tgtaaactaa tccgcaagtt   2580
ctttgagggc atcgcctcat tcgacatgca tagcgggaac atcatgttct caaatggaga   2640
cgtaccatac atcaccgacc cggtatcatt ctcgcagaag aaagacggtg gcgcattcag   2700
catcgaccct gaggaactca tcaaggaagt cgaggaagtc gcacgacaga agaaattga    2760 ccgcgctaag gcccgtaaag aacgtcacga ggggcgctta gaggcacgca gattcaaacg   2820
tcgcaaccgc aaggcacgta agcacacaa agctaagcgc gaaagaatgc ttgctgcgtg    2880
gcgatgggct gaacgtcaag aacggcgtaa ccatgaggta gctgtagatg tactaggaag   2940
aaccaataac gctatgctct gggtcaacat gttctctggg gactttaagg cgcttgagga   3000
acgaatcgcg ctgcactggc gtaatgctga ccggatggct atcgctaatg gtcttacgct   3060
```

```
caacattgat aagcaacttg acgcaatgtt aatgggctga tagtcttatc ttacaggtca    3120
tctgcgggtg gcctgaatag gtacgattta ctaactggaa gaggcactaa atgaacacga    3180
ttaacatcgc taagaacgac ttctctgaca tcgaactggc tgctatcccg ttcaacactc    3240
tggctgacca ttacggtgag cgtttagctc gcgaacagtt ggcccttgag catgagtctt    3300
acgagatggg tgaagcacgc ttccgcaaga tgtttgagcg tcaacttaaa gctggtgagg    3360
ttgcggataa cgctgccgcc aagcctctca tcactaccct actccctaag atgattgcac    3420
gcatcaacga ctggtttgag gaagtgaaag ctaagcgcgg caagcgcccg acagccttcc    3480
agttcctgca agaaatcaag ccggaagccg tagcgtacat caccattaag accactctgg    3540
cttgcctaac cagtgctgac aatacaaccg ttcaggctgt agcaagcgca atcggtcggg    3600
ccattgagga cgaggctcgc ttcggtcgta tccgtgacct tgaagctaag cacttcaaga    3660
aaaacgttga ggaacaactc aacaagcgcg tagggcacgt ctacaagaaa gcatttatgc    3720
aagttgtcga ggctgacatg ctctctaagg gtctactcgg tggcgaggcg tggtcttcgt    3780
ggcataagga agactctatt catgtaggag tacgctgcat cgagatgctc attgagtcaa    3840
ccggaatggt tagcttacac cgccaaaatg ctggcgtagt aggtcaagac tctgagacta    3900
tcgaactcgc acctgaatac gctgaggcta tcgcaacccg tgcaggtgcg ctggctggca    3960
tctctccgat gttccaacct tgcgtagttc tccctaagcc gtggactggc attactggtg    4020
gtggctattg ggctaacggt cgtcgtcctc tggcgctggt gcgtactcac agtaagaaag    4080
cactgatgcg ctacgaagac gtttacatgc ctgaggtgta caaagcgatt aacattgcgc    4140
aaaacaccgc atggaaaatc aacaagaaag tcctagcggt cgccaacgta atcaccaagt    4200
ggaagcattg tccggtcgag gacatccctg cgattgagcg tgaagaactc ccgatgaaac    4260
cggaagacat cgacatgaat cctgaggctc tcaccgcgtg gaaacgtgct gccgctgctg    4320
tgtaccgcaa ggacaaggct cgcaagtctc gccgtatcag ccttgagttc atgcttgagc    4380
aagccaataa gtttgctaac cataaggcca tctggttccc ttacaacatg gactggcgcg    4440
gtcgtgttta cgctgtgtca atgttcaacc cgcaaggtaa cgatatgacc aaaggactgc    4500
ttacgctggc gaaaggtaaa ccaatcggta aggaaggtta ctactggctg aaaatccacg    4560
gtgcaaactg tgcgggtgtc gataaggttc cgttccctga gcgcatcaag ttcattgagg    4620
aaaaccacga gaacatcatg gcttgcgcta agtctccact ggagaacact tggtgggctg    4680
agcaagattc tccgttctgc ttccttgcgt tctgctttga gtacgctggg gtacagcacc    4740
acggcctgag ctataactgc tcccttccgc tggcgtttga cggtcttgc tctggcatcc    4800
agcacttctc cgcgatgctc cgagatgagg taggtggtcg cgcggttaac ttgcttccta    4860
gtgaaaccgt tcaggacatc tacgggattg ttgctaagaa agtcaacgag attctacaag    4920
cagacgcaat caatgggacc gataacgaag tagttaccgt gaccgatgag aacactggtg    4980
aaatctctga gaaagtcaag ctgggcacta aggcactggc tggtcaatgg ctggcttacg    5040
gtgttactcg cagtgtgact aagcgttcag tcatgacgct ggcttacggg tccaaagagt    5100
tcggcttccg tcaacaagtg ctggaagata ccattcagcc agctattgat tccgcaagg    5160
gtctgatgtt cactcagccg aatcaggctg ctggatacat ggctaagctg atttgggaat    5220
ctgtgagcgt gacggtggta gctgcggttg aagcaatgaa ctggcttaag tctgctgcta    5280
agctgctggc tgctgaggtc aaagataaga agactggaga gattcttcgc aagcgttgcg    5340
ctgtgcattg ggtaactcct gatggtttcc ctgtgtggca ggaatacaag aagcctattc    5400
```

```
agacgcgctt gaacctgatg ttcctcggtc agttccgctt acagcctacc attaacacca      5460
acaaagatag cgagattgat gcacacaaac aggagtctgg tatcgctcct aactttgtac      5520
acagccaaga cggtagccac cttcgtaaga ctgtagtgtg ggcacacgag aagtacggaa      5580
tcgaatcttt tgcactgatt cacgactcct tcggtaccat tccggctgac gctgcgaacc      5640
tgttcaaagc agtgcgcgaa actatggttg acacatatga gtcttgtgat gtactggctg      5700
atttctacga ccagttcgct gaccagttgc acgagtctca attggacaaa atgccagcac      5760
ttccggctaa aggtaacttg aacctccgtg acatcttaga gtcggacttc gcgttcgcgt      5820
aacgccaaat caatacgact cactatagag ggacaaactc aaggtcattc gcaagagtgg      5880
cctttatgat tgaccttctt ccggttaata cgactcacta taggagaacc ttaaggttta      5940
actttaagac ccttaagtgt taattagaga tttaaattaa agaattacta agagaggact      6000
ttaagtatgc gtaacttcga aaagatgacc aaacgttcta accgtaatgc tcgtgacttc      6060
gaggcaacca aggtcgcaa gttgaataag actaagcgtg accgctctca caagcgtagc      6120
tgggagggtc agtaagatgg gacgtttata tagtggtaat ctggcagcat tcaaggcagc      6180
aacaaacaag ctgttccagt tagacttagc ggtcatttat gatgactggt atgatgccta      6240
tacaagaaaa gattgcatac ggttacgtat tgaggacagg agtggaaacc tgattgatac      6300
tagcaccttc taccaccacg acgaggacgt tctgttcaat atgtgtactg attggttgaa      6360
ccatatgtat gaccagttga aggactggaa gtaatacgac tcagtatagg acaatgctt      6420 aaggtcgctc tctaggagtg gccttagtca tttaaccaat aggagataaa cattatgatg      6480
aacattaaga ctaacccgtt taaagccgtg tctttcgtag agtctgccat taagaaggct      6540
ctggataacg ctgggtatct tatcgctgaa atcaagtacg atggtgtacg cgggaacatc      6600
tgcgtagaca atactgctaa cagttactgg ctctctcgtg tatctaaaac gattccggca      6660
ctggagcact taaacgggtt tgatgttcgc tggaagcgtc tactgaacga tgaccgttgc      6720
ttctacaaag atggctttat gcttgatggg gaactcatgg tcaagggcgt agactttaac      6780
acagggtccg gcctactgcg taccaaatgg actgacacga agaaccaaga gttccatgaa      6840
gagttattcg ttgaaccaat ccgtaagaaa gataaagttc cctttaagct gcacactgga      6900
caccttcaca taaaactgta cgctatcctc ccgctgcaca tcgtggagtc tggagaagac      6960
tgtgatgtca tgacgttgct catgcaggaa cacgttaaga acatgctgcc tctgctacag      7020
gaatacttcc ctgaaatcga atggcaagcg gctgaatctt acgaggtcta cgatatggta      7080
gaactacagc aactgtacga gcagaagcga gcagaaggcc atgagggtct cattgtgaaa      7140
gacccgatgt gtatctataa gcgcggtaag aaatctggct ggtggaaaat gaaacctgag      7200
aacgaagctg acggtatcat tcagggtctg tatgggtta caaaaggtct ggctaatgaa      7260
ggtaaagtga ttggttttga ggtgcttctt gagagtggtc gtttagttaa cgccacgaat      7320
atctctcgcg ccttaatgga tgagttcact gagacagtaa aagaggccac cctaagtcaa      7380
tggggattct ttagcccata cggtattggc gacaacgatg cttgtactat taacccttac      7440
gatggctggg cgtgtcaaat tagctacatg gaggaaacac ctgatggctc tttgcggcac      7500
ccatcgttcg taatgttccg tggcaccgag gacaaccctc aagagaaaat gtaatcacac      7560
tggctcacct tcgggtgggc ctttctgcgt ttataaggag acactttatg tttaagaagg      7620
ttggtaaatt ccttgcggct ttggcagcta tcctgacgct tgcgtatatt cttgcggtat      7680
accctcaagt agcactagta gtagttgcg cttgttactt agcggcagtg tgtgcttgcg      7740
tgtggagtat agttaactgg taatacgact cactaaagga ggtacacacc atgatgtact      7800
```

```
taatgccatt actcatcgtc attgtaggat gccttgcgct ccactgtagc gatgatgata   7860
tgccagatgg tcacgcttaa tacgactcac taaaggagac actatatgtt tcgacttcat   7920
tacaacaaaa gcgttaagaa tttcacggtt cgccgtgctg accgttcaat cgtatgtgcg   7980
agcgagcgcc gagctaagat acctcttatt ggtaacacag ttcctttggc accgagcgtc   8040
cacatcatta tcacccgtgg tgactttgag aaagcaatag acaagaaacg tccggttctt   8100
agtgtggcag tgacccgctt cccgttcgtc cgtctgttac tcaaacgaat caaggaggtg   8160
ttctgatggg actgttagat ggtgaagcct gggaaaaaga aaacccgcca gtacaagcaa   8220
ctgggtgtat agcttgctta gagaaagatg accgttatcc acacacctgt aacaaaggag   8280
ctaacgatat gaccgaacgt gaacaagaga tgatcattaa gttgatagac aataatgaag   8340
gtcgcccaga tgatttgaat ggctgcggta ttctctgctc caatgtccct tgccacctct   8400
gccccgcaaa taacgatcaa aagataacct taggtgaaat ccgagcgatg acccacgta    8460
aaccacatct gaataaacct gaggtaactc ctacagatga ccagccttcc gctgagacaa   8520
tcgaaggtgt cactaagcct tcccactaca tgctgtttga cgacattgag gctatcgaag   8580
tgattgctcg ttcaatgacc gttgagcagt tcaagggata ctgcttcggt aacatcttaa   8640
agtacagact acgtgctggt aagaagtcag agttagcgta cttagagaaa gacctagcga   8700
aagcagactt ctataaagaa ctctttgaga aacataagga taaatgttat gcataacttc   8760
aagtcaaccc cacctgccga cagcctatct gatgacttca catcttgctc agagtggtgc   8820
cgaaagatgt gggaagagac attcgacgat gcgtacatca agctgtatga actttggaaa   8880
tcgagaggtc aatgactatg tcaaacgtaa atacaggttc acttagtgtg gacaataaga   8940
agttttgggc taccgtagag tcctcggagc attccttcga ggttccaatc tacgctgaga   9000
ccctagacga agctctggag ttagccgaat ggcaatacgt tccggctggc tttgaggtta   9060
ctcgtgtgcg tccttgtgta gcaccgaagt aatacgactc actattaggg aagactccct   9120
ctgagaaacc aaacgaaacc taaaggagat taacattatg gctaagaaga ttttcacctc   9180
tgcgctgggt accgctgaac cttacgctta catcgccaag ccggactacg caacgaaga    9240
gcgtggcttt gggaaccctc gtggtgtcta taaagttgac ctgactattc caacaaaga    9300
cccgcgctgc cagcgtatgg tcgatgaaat cgtgaagtgt cacgaagagg cttatgctgc   9360
tgccgttgag gaatacgaag ctaatccacc tgctgtagct cgtggtaaga accgctgaa    9420
accgtatgag ggtgacatgc cgttcttcga taacggtgac ggtacgacta cctttaagtt   9480
caaatgctac gcgtctcttcc aagacaagaa gaccaaagag accaagcaca tcaatctggt   9540
tgtggttgac tcaaaaggta agaagatgga agacgttccg attatcggtg gtggctctaa   9600
gctgaaagtt aaatattctc tggttccata caagtggaac actgctgtag gtgcgagcgt   9660
taagctgcaa ctggaatccg tgatgctggt cgaactggct acctttggtg gcggtgaaga   9720
cgattgggct gacgaagttg aagagaacgg ctatgttgcc tctggttctg ccaaagcgag   9780
caaaccacgc gacgaagaaa gctgggacga agacgacgaa gagtccgagg aagcagacga   9840
agacggagac ttctaagtgg aactgcggga gaaaatcctt gagcgaatca aggtgacttc   9900
ctctgggtgt tgggagtggc agggcgctac gaacaataaa gggtacgggc aggtgtggtg   9960
cagcaatacc ggaaaggttg tctactgtca tcgcgtaatg tctaatgctc cgaaaggttc   10020
taccgtcctg cactcctgtg ataatccatt atgttgtaac cctgaacacc tatccatagg   10080
aactccaaaa gagaactcca ctgacatggt aaataagggt cgctcacaca aggggtataa   10140
```

```
actttcagac gaagacgtaa tggcaatcat ggagtccagc gagtccaatg tatccttagc   10200
tcgcacctat ggtgtctccc aacagactat ttgtgatata cgcaaaggga ggcgacatgg   10260
caggttacgg cgctaaagga atccgaaagg ttggagcgtt tcgctctggc ctagaggaca   10320
aggtttcaaa gcagttggaa tcaaaaggta ttaaattcga gtatgaagag tggaaagtgc   10380
cttatgtaat tccggcgagc aatcacactt acactccaga cttcttactt ccaaacggta   10440
tattcgttga gacaaagggt ctgtgggaaa gcgatgatag aaagaagcac ttattaatta   10500
gggagcagca ccccgagcta gacatccgta ttgtcttctc aagctcacgt actaagttat   10560
acaaaggttc tccaacgtct tatggagagt tctgcgaaaa gcatggtatt aagttcgctg   10620
ataaactgat acctgctgag tggataaagg aacccaagaa ggaggtcccc tttgatagat   10680 taaaaggaa aggaggaaag aaataatggc tcgtgtacag tttaaacaac gtgaatctac   10740
tgacgcaatc tttgttcact gctcggctac caagccaagt cagaatgttg gtgtccgtga   10800
gattcgccag tggcacaaag agcagggttg gctcgatgtg ggataccact ttatcatcaa   10860
gcgagacggt actgtggagg caggacgaga tgagatggct gtaggctctc acgctaaggg   10920
ttacaaccac aactctatcg gcgtctgcct tgttggtggt atcgacgata aaggtaagtt   10980
cgacgctaac tttacgccag cccaaatgca atcccttcgc tcactgcttg tcacactgct   11040
ggctaagtac gaaggcgctg tgcttcgcgc ccatcatgag gtggcgccga aggcttgccc   11100
ttcgttcgac cttaagcgtt ggtgggagaa gaacgaactg gtcacttctg accgtggata   11160
attaattgaa ctcactaaag ggagaccaca gcggtttccc tttgttcgca ttggaggtca   11220
aataatgcgc aagtcttata aacaattcta taaggctccg aggaggcata tccaagtgtg   11280
ggaggcagcc aatgggccta taccaaaagg ttattatata gaccacattg acggcaatcc   11340
actcaacgac gccttagaca atctccgtct ggctctccca aaagaaaact catgaacat   11400 gaagactcca agagcaata cctcaggact aaagggactg agttggagca aggaaaggga   11460
gatgtggaga ggcactgtaa cagctgaggg taaacagcat aactttcgta gtagagatct   11520
attggaagtc gttgcgtgga tttatagaac taggagggaa ttgcatggac aattcgcacg   11580
attccgatag tgtatttctt taccacattc cttgtgacaa ctgtgggagt agtgatggga   11640
actcgctgtt ctctgacgga cacacgttct gctacgtatg cgagaagtgg actgctggta   11700
atgaagacac taaagagagg gcttcaaaac ggaaaccctc aggaggtaaa ccaatgactt   11760
acaacgtgtg gaacttcggg gaatccaatg gacgctactc cgcgttaact gcgagaggaa   11820
tctccaagga aacctgtcag aaggctggct actggattgc caaagtagac ggtgtgatgt   11880
accaagtggc tgactatcgg gaccagaacg gcaacattgt gagtcagaag gttcgagata   11940
aagataagaa ctttaagacc actggtagtc acaagagtga cgctctgttc gggaagcact   12000
tgtggaatgg tggtaagaag attgtcgtta cagaaggtga aatcgacatg cttaccgtga   12060
tggaacttca agactgtaag tatcctgtag tgtcgttggg tcacggtgcc tctgccgcta   12120
agaagacatg cgctgccaac tacgaatact ttgaccagtt cgaacagatt atcttaatgt   12180
tcgatatgga cgaagcaggg cgcaaagcag tcgaagaggc tgcacaggtt ctacctgctg   12240
gtaaggtacg agtggcagtt cttccgtgta aggatgcaaa cgagtgtcac ctaaatggtc   12300
acgaccgtga atcatggag caagtgtgga atgctggtcc ttggattcct gatggtgtgg   12360
tatcggctct ttcgttacgt gaacgaatcc gtgagcacct atcgtccgag gaatcagtag   12420
gtttactttt cagtggctgc actggtatca acgataagac cttaggtgcc cgtggtggtc   12480
aagtcattat ggtcacttcc ggttccggta tgggtaagtc aacgttcgtc cgtcaacaag   12540
```

```
ctctacaatg gggcacagcg atgggcaaga aggtaggctt agcgatgctt gaggagtccg   12600
ttgaggagac cgctgaggac cttataggtc tacacaaccg tgtccgactg agacaatccg   12660
actcactaaa gagagagatt attgagaacg gtaagttcga ccaatggttc gatgaactgt   12720
tcggcaacga tacgttccat ctatatgact cattcgccga ggctgagacg gatagactgc   12780
tcgctaagct ggcctacatg cgctcaggct tgggctgtga cgtaatcatt ctagaccaca   12840
tctcaatcgt cgtatccgct tctggtgaat ccgatgagcg taagatgatt gacaacctga   12900
tgaccaagct caaagggttc gctaagtcaa ctggggtggt gctggtcgta atttgtcacc   12960
ttaagaaccc agacaaaggt aaagcacatg aggaaggtcg ccccgtttct attactgacc   13020
tacgtggttc tggcgcacta cgccaactat ctgatactat tattgcccct gagcgtaatc   13080
agcaaggcga tatgcctaac cttgtcctcg ttcgtattct caagtgccgc tttactggtg   13140
atactggtat cgctggctac atggaataca acaaggaaac cggatggctt gaaccatcaa   13200
gttactcagg ggaagaagag tcacactcag agtcaacaga ctggtccaac gacactgact   13260
tctgacagga ttcttgatga cttttccagac gactacgaga agtttcgctg gagagtccca   13320
ttctaatacg actcactaaa ggagacacac catgttcaaa ctgattaaga agttaggcca   13380
actgctggtt cgtatgtaca acgtggaagc caagcgactg aacgatgagg ctcgtaaaga   13440
ggccacacag tcacgcgctc tggcgattcg ctccaacgaa ctggctgaca gtgcatccac   13500
taaagttacc gaggctgccc gtgtggcaaa ccaagctcaa cagcttttcca aattctttga   13560 gtaatcaaac aggagaaacc attatgtcta acgtagctga aactatccgt ctatccgata   13620
cagctgacca gtggaaccgt cgagtccaca tcaacgttcg caacggtaag gcgactatgg   13680
tttaccgctg gaaggactct aagtcctcta agaatcacac tcagcgtatg acgttgacag   13740
atgagcaagc actgcgtctg gtcaatgcgc ttaccaaagc tgccgtgaca gcaattcatg   13800
aagctggtcg cgtcaatgaa gctatggcta tcctcgacaa gattgataac taagagtggt   13860
atcctcaagg tcgccaaagt ggtggccttc atgaatacta ttcgactcac tataggagat   13920
attaccatgc gtgaccctaa agttatccaa gcagaaatcg ctaaactgga agctgaactg   13980
gaggacgtta agtaccatga agctaagact cgctccgctg ttcacatctt gaagaactta   14040
ggctggactt ggacaagaca gactggctgg aagaaaccag aagttaccaa gctgagtcat   14100
aaggtgttcg ataaggacac tatgacccac atcaaggctg gtgattgggt taaggttgac   14160
atgggagttg ttggtggata cggctacgtc cgctcagtta gtggcaaata tgcacaagtg   14220
tcatacatca caggtgttac tccacgcggt gcaatcgttg ccgataagac caacatgatt   14280
cacacaggtt tcttgacagt tgtttcatat gaagagattg ttaagtcacg ataatcaata   14340
ggagaaatca atatgatcgt ttctgacatc gaagctaacg ccctcttaga gagcgtcact   14400
aagttccact gcggggttat ctacgactac tccaccgctg agtacgtaag ctaccgtccg   14460
agtgacttcg gtgcgtatct ggatgcgctg gaagccgagg ttgcacgagg cggtcttatt   14520
gtgttccaca acggtcacaa gtatgacgtt cctgcattga ccaaactggc aaagttgcaa   14580
ttgaaccgag agttccacct tcctcgtgag aactgtattg acacccttgt gttgtcacgt   14640
ttgattcatt ccaacctcaa ggacaccgat atgggtcttc tgcgttccgg caagttgccc   14700
ggaaaacgct ttgggtctca cgctttggag gcgtggggtt atcgcttagg cgagatgaag   14760
ggtgaataca aagacgactt taagcgtatg cttgaagagc agggtgaaga atacgttgac   14820
ggaatggagt ggtggaactt caacgaagag atgatggact ataacgttca ggacgttgtg   14880
```

```
gtaactaaag ctctccttga gaagctactc tctgacaaac attacttccc tcctgagatt    14940
gactttacgg acgtaggata cactacgttc tggtcagaat cccttgaggc cgttgacatt    15000
gaacatcgtg ctgcatggct gctcgctaaa caagagcgca acgggttccc gtttgacaca    15060
aaagcaatcg aagagttgta cgtagagtta gctgctcgcc gctctgagtt gctccgtaaa    15120
ttgaccgaaa cgttcggctc gtggtatcag cctaaaggtg gcactgagat gttctgccat    15180
ccgcgaacag gtaagccact acctaaatac cctcgcatta agacacctaa agttggtggt    15240
atctttaaga agcctaagaa caaggcacag cgagaaggcc gtgagccttg cgaacttgat    15300
acccgcgagt acgttgctgg tgctccttac accccagttg aacatgttgt gtttaaccct    15360
tcgtctcgtg accacattca gaagaaactc caagaggctg ggtgggtccc gaccaagtac    15420
accgataagg gtgctcctgt ggtggacgat gaggtactcg aaggagtacg tgtagatgac    15480
cctgagaagc aagccgctat cgacctcatt aaagagtact tgatgattca gaagcgaatc    15540
ggacagtctg ctgagggaga caaagcatgg cttcgttatg ttgctgagga tggtaagatt    15600
catggttctg ttaaccctaa tggagcagtt acgggtcgtg cgacccatgc gttcccaaac    15660
cttgcgcaaa ttccgggtgt acgttctcct tatggagagc agtgtcgcgc tgcttttggc    15720
gctgagcacc atttggatgg gataactggt aagccttggg ttcaggctgg catcgacgca    15780
tccggtcttg agctacgctg cttggctcac ttcatggctc gctttgataa cggcgagtac    15840
gctcacgaga ttcttaacgg cgacatccac actaagaacc agatagctgc tgaactacct    15900
acccgagata cgctaagac gttcatctat gggttcctct atggtgctgg tgatgagaag    15960
attggacaga ttgttggtgc tggtaaagag cgcggtaagg aactcaagaa gaaattcctt    16020
gagaacaccc ccgcgattgc agcactccgc gagtctatcc aacagacact tgtcgagtcc    16080
tctcaatggg tagctggtga gcaacaagtc aagtggaaac gccgctggat taaaggtctg    16140
gatggtcgta aggtacacgt tcgtagtcct cacgctgcct tgaatacccct actgcaatct    16200
gctggtgctc tcatctgcaa actgtggatt atcaagaccg aagagatgct cgtagagaaa    16260
ggcttgaagc atggctggga tggggacttt gcgtacatgg catgggtaca tgatgaaatc    16320
caagtaggct gccgtaccga agagattgct caggtggtca ttgagaccgc acaagaagcg    16380
atgcgctggg ttggagacca ctggaacttc cggtgtcttc tggataccga aggtaagatg    16440
ggtcctaatt gggcgatttg ccactgatac aggaggctac tcatgaacga agcacttaa    16500
acaggtgctg cttctgaaat gctagtagcc tacaaattta ccaaagctgg gtacactgtc    16560
tattacccta tgctgactca gagtaaagag gacttggttg tatgtaagga tggtaaatttt    16620
agtaaggttc aggttaaaac agccacaacg gttcaaacca acacaggaga tgccaagcag    16680
gttaggctag gtgatgcgg taggtccgaa tataaggatg gagactttga cattcttgcg    16740
gttgtggttg acgaagatgt gcttattttc acatgggacg aagtaaaagg taagacatcc    16800
atgtgtgtcg gcaagagaaa caaaggcata aaactatagg agaaattatt atggctatga    16860
caaagaaatt taaagtgtcc ttcgacgtta ccgcaaagat gtcgtctgac gttcaggcaa    16920
tcttagagaa agatatgctg catctatgta agcaggtcgg ctcaggtgcg attgtcccca    16980
atggtaaaca gaaggaaatg attgtccagt tcctgacaca cggtatggaa ggattgatga    17040
cattcgtagt acgtacatca tttcgtgagg ccattaagga catgcacgaa gagtatgcag    17100
ataaggactc tttcaaacaa tctcctgcaa cagtacggga ggtgttctga tgtctgacta    17160
cctgaaagtg ctgcaagcaa tcaaaagttg ccctaagact ttccagtcca actatgtacg    17220
gaacaatgcg agcctcgtag cggaggccgc ttcccgtggt cacatctcgt gcctgactac    17280
```

```
tagtggacgt aacggtggcg cttgggaaat cactgcttcc ggtactcgct ttctgaaacg   17340
aatgggagga tgtgtctaat gtctcgtgac cttgtgacta ttccacgcga tgtgtggaac   17400
gatatacagg gctacatcga ctctctggaa cgtgagaacg atagccttaa gaatcaacta   17460
atggaagctg acgaatacgt agcggaacta gaggagaaac ttaatggcac ttcttgacct   17520
taaacaattc tatgagttac gtgaaggctg cgacgacaag ggtatccttg tgatggacgg   17580
cgactggctg gtcttccaag ctatgagtgc tgctgagttt gatgcctctt ggaggaagaa   17640
gatttggcac cgatgctgtg accacgctaa ggcccgtcag attcttgagg attccattaa   17700
gtcctacgag acccgtaaga aggcttgggc aggtgctcca attgtccttg cgttcaccga   17760
tagtgttaac tggcgtaaag aactggttga cccgaactat aaggctaacc gtaaggccgt   17820
gaagaaacct gtagggtact ttgagttcct tgatgctctc tttgagcgcg aagagttcta   17880
ttgcatccgt gagcctatgc ttgagggtga tgacgttatg ggagttattg cttccaatcc   17940
gtctgccttc ggtgctcgta aggctgtaat catctcttgc gataaggact ttaagaccat   18000
ccctaactgt gacttcctgt ggtgtaccac tggtaacatc ctgactcaga ccgaagagtc   18060
cgctgactgt tggcacctct tccagaccat caagggtgac atcactgatg ttactcagg   18120 gattgctgga tggggtgata ccgccgagga cttcttgaat aacccgttca taaccgagcc   18180
taaaacgtct gtgcttaagt ccggtaagaa caaaggccaa gaggttacta atgggttaa   18240 acgcgaccct gagcctcatg agacgctttg ggactgcatt aagtccattg gcgcgaaggc   18300
tggtatgacc gaagaggata ttatcaagca gggccaaatg gctcgaatcc tacggttcaa   18360
cgagtacaac tttattgaca aggagattta cctgtggaga ccgtagcgta tattggtctg   18420
ggtctttgtg ttctcggagt gtgcctcatt tcgtggggcc tttgggactt agccagaata   18480
atcaagtcgt tacacgacac taagtgataa actcaaggtc cctaaattaa tacgactcac   18540
tatagggaga taggggcctt tacgattatt actttaagat ttaactctaa gaggaatctt   18600
tattatgtta acacctatta accaattact taagaaccct aacgatattc cagatgtacc   18660
tcgtgcaacc gctgagtatc tacaggttcg attcaactat gcgtacctcg aagcgtctgg   18720
tcatatagga cttatgcgtg ctaatggttg tagtgaggcc cacatcttgg gtttcattca   18780
gggcctacag tatgcctcta cgtcattga cgagattgag ttacgcaagg aacaactaag   18840
agatgatggg gaggattgac actatgtgtt tctcaccgaa aattaaaact ccgaagatgg   18900
ataccaatca gattcgagcc gttgagccag cgcctctgac ccaagaagtg tcaagcgtgg   18960
agttcggtgg gtcttctgat gagacggata ccgagggcac cgaagtgtct ggacgcaaag   19020
gcctcaaggt cgaacgtgat gattccgtag cgaagtctaa agccagcggc aatggctccg   19080
ctcgtatgaa atcttccatc cgtaagtccg catttggagg taagaagtga tgtctgagtt   19140
cacatgtgtg gaggctaaga gtcgcttccg tgcaatccgg tggactgtgg aacaccttgg   19200
gttgcctaaa ggattcgaag gacactttgt gggctacagc ctctacgtag acgaagtgat   19260
ggacatgtct ggttgccgtg aagagtacat tctggactct accggaaaac atgtagcgta   19320
cttcgcgtgg tgcgtaagct gtgacattca ccacaaagga gacattctgg atgtaacgtc   19380
cgttgtcatt aatcctgagg cagactctaa gggcttacag cgattcctag cgaaacgctt   19440
taagtacctt gcggaactcc acgattgcga ttgggtgtct cgttgtaagc atgaaggcga   19500
gacaatgcgt gtatacttta aggaggtata agttatgggt aagaaagtta agaaggccgt   19560
gaagaaagtc accaagtccg ttaagaaagt cgttaaggaa ggggctcgtc cggttaaaca   19620
```

```
ggttgctggc ggtctagctg gtctggctgg tggtactggt gaagcacaga tggtggaagt    19680
accacaagct gccgcacaga ttgttgacgt acctgagaaa gaggtttcca ctgaggacga    19740
agcacagaca gaaagcggac gcaagaaagc tcgtgctggc ggtaagaaat ccttgagtgt    19800
agcccgtagc tccggtggcg gtatcaacat ttaatcagga ggttatcgtg aagactgca     19860 ttgaatggac cggaggtgtc aactctaagg gttatggtcg taagtgggtt aatggtaaac    19920
ttgtgactcc acataggcac atctatgagg agacatatgg tccagttcca acaggaattg    19980
tggtgatgca tatctgcgat aaccctaggt gctataacat aaagcacctt acgcttggaa    20040
ctccaaagga taattccgag gacatggtta ccaaaggtag acaggctaaa ggagaggaac    20100
taagcaagaa acttacagag tcagacgttc tcgctatacg ctcttcaacc ttaagccacc    20160
gctccttagg agaactgtat ggagtcagtc aatcaaccat aacgcgaata ctacagcgta    20220
agacatggag acacatttaa tggctgagaa acgaacagga cttgcggagg atggcgcaaa    20280
gtctgtctat gagcgtttaa agaacgaccg tgctccctat gagacacgcg ctcagaattg    20340
cgctcaatat accatcccat cattgttccc taaggactcc gataacgcct ctacagatta    20400
tcaaactccg tggcaagccg tgggcgctcg tggtctgaac aatctagcct ctaagctcat    20460
gctggctcta ttccctatgc agacttggat gcgacttact atatctgaat atgaagcaaa    20520
gcagttactg agcgaccccg atggactcgc taaggtcgat gagggcctct cgatggtaga    20580
gcgtatcatc atgaactaca ttgagtctaa cagttaccgc gtgactctct ttgaggctct    20640
caaacagtta gtcgtagctg gtaacgtcct gctgtaccta ccggaaccgg aagggtcaaa    20700
ctataatccc atgaagctgt accgattgtc ttcttatgtg gtccaacgag acgcattcgg    20760
caacgttctg caaatggtga ctcgtgacca gatagctttt ggtgctctcc ctgaggacat    20820
ccgtaaggct gtagaaggtc aaggtggtga agaaaagct gatgagacaa tcgacgtgta    20880
cactcacatc tatctggatg aggactcagg tgaataccctc cgatacgaag aggtcgaggg    20940 tatgaagtc caaggctccg atgggactta tcctaaagag gcttgcccat acatcccgat    21000
tcggatggtc agactagatg gtgaatccta cggtcgttcg tacattgagg aatacttagg    21060
tgacttacgg tcccttgaaa atctccaaga ggctatcgtc aagatgtcca tgattagctc    21120
taaggttatc ggcttagtga atcctgctgg tatcacccag ccacgccgac tgaccaaagc    21180
tcagactggt gacttcgtta ctggtcgtcc agaagacatc tcgttcctcc aactggagaa    21240
gcaagcagac tttactgtag ctaaagccgt aagtgacgct atcgaggctc gcctttcgtt    21300
tgcctttatg ttgaactctg cggttcagcg tacaggtgaa cgtgtgaccg ccgaagagat    21360
tcggtatgta gcttctgaac ttgaagatac tttaggtggt gtctactcta tcctttctca    21420
agaattacaa ttgcctctgg tacgagtgct cttgaagcaa ctacaagcca cgcaacagat    21480
tcctgagtta cctaaggaag ccgtagagcc aaccattagt acaggtctgg aagcaattgg    21540
tcgaggacaa gaccttgata agctggagcg gtgtgtcact gcgtgggctg cactggcacc    21600
tatgcgggac gaccctgata ttaaccttgc gatgattaag ttacgtattg ccaacgctat    21660
cggtattgac acttctggta ttctactcac cgaagaacag aagcaacaga agatggccca    21720
acagtctatg caaatgggta tggataatgg tgctgctgcg ctggctcaag gtatggctgc    21780
acaagctaca gcttcacctg aggctatggc tgctgccgct gattccgtag gttttacagcc   21840 gggaatttaa tacgactcac tatagggaga cctcatcttt gaaatgagcg atgacaagag    21900
gttggagtcc tcggtcttcc tgtagttcaa ctttaaggag acaataataa tggctgaatc    21960
taatgcagac gtatatgcat cttttggcgt gaactccgct gtgatgtctg gtggttccgt    22020
```

```
tgaggaacat gagcagaaca tgctggctct tgatgttgct gcccgtgatg gcgatgatgc   22080
aatcgagtta gcgtcagacg aagtggaaac agaacgtgac ctgtatgaca actctgaccc   22140
gttcggtcaa gaggatgacg aaggccgcat tcaggttcgt atcggtgatg gctctgagcc   22200
gaccgatgtg gacactggag aagaaggcgt tgagggcacc gaaggttccg aagagtttac   22260
cccactgggc gagactccag aagaactggt agctgcctct gagcaacttg gtgagcacga   22320
agagggcttc caagagatga ttaacattgc tgctgagcgt ggcatgagtg tcgagaccat   22380
tgaggctatc cagcgtgagt acgaggagaa cgaagagttg tccgccgagt cctacgctaa   22440
gctggctgaa attggctaca cgaaggcttt cattgactcg tatatccgtg gtcaagaagc   22500
tctggtggag cagtacgtaa acagtgtcat tgagtacgct ggtggtcgtg aacgttttga   22560
tgcactgtat aaccaccttg agacgcacaa ccctgaggct gcacagtcgc tggataatgc   22620
gttgaccaat cgtgacttag cgaccgttaa ggctatcatc aacttggctg gtgagtctcg   22680
cgctaaggcg ttcggtcgta agccaactcg tagtgtgact aatcgtgcta ttccggctaa   22740
acctcaggct accaagcgtg aaggctttgc ggaccgtagc gagatgatta aagctatgag   22800
tgaccctcgg tatcgcacag atgccaacta tcgtcgtcaa gtcgaacaga agtaatcga   22860 ttcgaacttc tgatagactt cgaaattaat acgactcact atagggagac cacaacggtt   22920
tccctctaga ataattttg tttaacttta agaaggagat atacatatgg ctagcatgac   22980
tggtggacag caaatgggta ctaaccaagg taaaggtgta gttgctgctg gagataaact   23040
ggcgttgttc ttgaaggtat ttggcggtga agtcctgact gcgttcgctc gtacctccgt   23100
gaccacttct cgccacatgg tacgttccat ctccagcggt aaatccgctc agttccctgt   23160
tctgggtcgc actcaggcag cgtatctggc tccgggcgag aacctcgacg ataaacgtaa   23220
ggacatcaaa cacaccgaga aggtaatcac cattgacggt ctcctgacgg ctgacgttct   23280
gatttatgat attgaggacg cgatgaacca ctacgacgtt cgctctgagt ataccctctca   23340 gttgggtgaa tctctggcga tggctgcgga tggtgcggtt ctggctgaga ttgccggtct   23400
gtgtaacgtg gaaagcaaat ataatgaaa catcgagggc ttaggtactg ctaccgtaat   23460
tgagaccact cagaacaagg ccgcacttac cgaccaagtt gcgctgggta aggagattat   23520
tgcggctctg actaaggctc gtgcggctct gaccaagaac tatgttccgg ctgctgaccg   23580
tgtgttctac tgtgacccag atagctactc tgcgattctg cagcactga tgccgaacgc   23640 agcaaaactac gctgctctga ttgaccctga aagggttct atccgcaacg ttatgggctt   23700
tgaggttgta gaagttccgc acctcaccgc tggtggtgct ggtaccgctc gtgagggcac   23760
tactggtcag aagcacgtct tccctgccaa taaaggtgag ggtaatgtca aggttgctaa   23820
ggacaacgtt atcggcctgt tcatgcaccg ctctgcggta ggtactgtta agctgcgtga   23880
cttggctctg gagcgcgctc gccgtgctaa cttccaagcg gaccagatta tcgctaagta   23940
cgcaatgggc cacggtggtc ttcgcccaga agctgctggt gcagtggttt tcaaagtgga   24000
gtaatgctgg gggtggcctc aacggtcgct gctagtcccg aagaggcgag tgttacttca   24060
acagaagaaa ccttaacgcc agcacaggag gccgcacgca cccgcgctgc taacaaagcc   24120
cgaaaggaag ctgagttggc tgctgccacc gctgagcaat aactagcata ccccttggg   24180 gcctctaaac gggtcttgag gggttttttg ctgaaaggag gaactatatg cgctcatacg   24240
atatgaacgt tgagactgcc gctgagttat cagctgtgaa cgacattctg cgtctatcg   24300 gtgaacctcc ggtatcaacg ctggaaggtg acgctaacgc agatgcagcg aacgctcggc   24360
```

```
gtattctcaa caagattaac cgacagattc aatctcgtgg atggacgttc aacattgagg    24420
aaggcataac gctactacct gatgtttact ccaacctgat tgtatacagt gacgactatt    24480
tatccctaat gtctacttcc ggtcaatcca tctacgttaa ccgaggtggc tatgtgtatg    24540
accgaacgag tcaatcagac cgctttgact ctggtattac tgtgaacatt attcgtctcc    24600
gcgactacga tgagatgcct gagtgcttcc gttactggat tgtcaccaag gcttcccgtc    24660
agttcaacaa ccgattcttt ggggcaccgg aagtagaggg tgtactccaa gaagaggaag    24720
atgaggctag acgtctctgc atggagtatg agatggacta cggtgggtac aatatgctgg    24780
atggagatgc gttcacttct ggtctactga ctcgctaaca ttaataaata aggaggctct    24840
aatggcactc attagccaat caatcaagaa cttgaagggt ggtatcagcc aacagcctga    24900
catccttcgt tatccagacc aagggtcacg ccaagttaac ggttggtctt cggagaccga    24960
gggcctccaa aagcgtccac ctcttgtttt cttaaataca cttggagaca acggtgcgtt    25020
aggtcaagct ccgtacatcc acctgattaa ccgagatgag cacgaacagt attacgctgt    25080
gttcactggt agcggaatcc gagtgttcga cctttctggt aacgagaagc aagttaggta    25140
tcctaacggt tccaactaca tcaagaccgc taatccacgt aacgacctgc gaatggttac    25200
tgtagcagac tatacgttca tcgttaaccg taacgttgtt gcacagaaga acacaaagtc    25260
tgtcaactta ccgaattaca ccctaatca agacggattg attaacgttc gtggtggtca    25320
gtatggtagg gaactaattg tacacattaa cggtaaagac gttgcgaagt ataagatacc    25380
agatggtagt caacctgaac acgtaaacaa tacggatgcc caatggttag ctgaagagtt    25440
agccaagcag atgcgcacta acttgtctga ttggactgta aatgtagggc aagggttcat    25500
ccatgtgacc gcacctagtg gtcaacagat tgactccttc acgactaaag atggctacgc    25560
agaccagttg attaaccctg tgacccacta cgctcagtcg ttctctaagc tgccacctaa    25620
tgctcctaac ggctacatgg tgaaaatcgt aggggacgcc tctaagtctg ccgaccagta    25680
ttacgttcgg tatgacgctg agcggaaagt ttggactgag actttaggtt ggaacactga    25740
ggaccaagtt ctatgggaaa ccatgccaca cgctcttgtg cgagccgctg acggtaattt    25800
cgacttcaag tggcttgagt ggtctcctaa gtcttgtggt gacgttgaca ccaacccttg    25860
gccttctttt gttggttcaa gtattaacga tgtgttcttc ttccgtaacc gcttaggatt    25920
ccttagtggg gagaacatca tattgagtcg tacagccaaa tacttcaact tctaccctgc    25980
gtccattgcg aaccttagtg atgacgaccc tatagacgta gctgtgagta ccaaccgaat    26040
agcaatcctt aagtacgccg ttccgttctc agaagagtta ctcatctggt ccgatgaagc    26100
acaattcgtc ctgactgcct cgggtactct cacatctaag tcggttgagt tgaacctaac    26160
gacccagttt gacgtacagg accgagcgag acctttgggg attgggcgta atgtctactt    26220
tgctagtccg aggtccagct tcacgtccat ccacaggtac tacgctgtgc aggatgtcag    26280
ttccgttaag aatgctgagg acattacatc acacgttcct aactacatcc ctaatggtgt    26340
gttcagtatt tgcggaagtg gtacggaaaa cttctgttcg gtactatctc acggggaccc    26400
tagtaaaatc ttcatgtaca aattcctgta cctgaacgaa gagttaaggc aacagtcgtg    26460
gtctcattgg gactttgggg aaaacgtaca ggttctagct tgtcagagta tcagctcaga    26520
tatgtatgtg attcttcgca atgagttcaa tacgttccta gctagaatct ctttcactaa    26580
gaacgccatt gacttacagg agaaccccta tcgtgccttt atggacatga agattcgata    26640
cacgattcct agtggaacat acaacgatga cacattcact acctctattc atattccaac    26700
aatttatggt gcaaacttcg ggagggggcaa aatcactgta ttggagcctg atggtaagat    26760
```

```
aaccgtgttt gagcaaccta cggctgggtg gaatagcgac ccttggctga gactcagcgg    26820
taacttggag ggacgcatgg tgtacattgg gttcaacatt aacttcgtat atgagttctc    26880
taagttcctc atcaagcaga ctgccgacga cgggtctacc tccacggaag acattgggcg    26940
cttacagtta cgccgagcgt gggttaacta cgagaactct ggtacgtttg acatttatgt    27000
tgagaaccaa tcgtctaact ggaagtacac aatggctggt gcccgattag gctctaacac    27060
tctgagggct gggagactga acttagggac cggacaatat cgattccctg tggttggtaa    27120
cgccaagttc aacactgtat acatcttgtc agatgagact acccctctga acatcattgg    27180
gtgtggctgg gaaggtaact acttacggag aagttccggt atttaattaa atattctccc    27240
tgtggtggct cgaaattaat acgactcact atagggagaa caatacgact acgggagggt    27300
tttcttatga tgactataag acctactaaa agtacagact ttgaggtatt cactccggct    27360
caccatgaca ttcttgaagc taaggctgct ggtattgagc cgagtttccc tgatgcttcc    27420
gagtgtgtca cgttgagcct ctatgggttc cctctagcta tcggtggtaa ctgcggggac    27480
cagtgctggt tcgttacgag cgaccaagtg tggcgactta gtggaaaggc taagcgaaag    27540
ttccgtaagt taatcatgga gtatcgcgat aagatgcttg agaagtatga tactctttgg    27600
aattacgtat gggtaggcaa tacgtcccac attcgtttcc tcaagactat cggtgcggta    27660
ttccatgaag agtacacacg agatggtcaa tttcagttat ttacaatcac gaaaggagga    27720
taaccatatg tgttgggcag ccgcaatacc tatcgctata tctggcgctc aggctatcag    27780
tggtcagaac gctcaggcca aaatgattgc cgctcagacc gctgctggtc gtcgtcaagc    27840
tatggaaatc atgaggcaga cgaacatcca gaatgctgac ctatcgttgc aagctcgaag    27900
taaacttgag gaagcgtccg ccgagttgac ctcacagaac atgcagaagg tccaagctat    27960
tgggtctatc cgagcggcta tcggagagag tatgcttgaa ggttcctcaa tggaccgcat    28020
taagcgagtc acagaaggac agttcattcg ggaagccaat atggtaactg agaactatcg    28080
ccgtgactac caagcaatct tcgcacagca acttggtggt actcaaagtg ctgcaagtca    28140
gattgacgaa atctataaga gcgaacagaa acagaagagt aagctacaga tggttctgga    28200
cccactggct atcatggggt cttccgctgc gagtgcttac gcatccggtg cgttcgactc    28260
taagtccaca actaaggcac ctattgttgc cgctaaagga accaagacgg ggaggtaatg    28320
agctatgagt aaaattgaat ctgcccttca agcggcacaa ccgggactct ctcggttacg    28380
tggtggtgct ggaggtatgg gctatcgtgc agcaaccact caggccgaac agccaaggtc    28440
aagcctattg gacaccattg gtcggttcgc taaggctggt gccgatatgt ataccgctaa    28500
ggaacaacga gcacgagacc tagctgatga acgctctaac gagattatcc gtaagctgac    28560
ccctgagcaa cgtcgagaag ctctcaacaa cgggacccct ctgtatcagg atgacccata    28620
cgctatggaa gcactccgag tcaagactgg tcgtaacgct gcgtatcttg tggacgatga    28680
cgttatgcag aagataaaag agggtgtctt ccgtactcgc gaagagatgg aagagtatcg    28740
ccatagtcgc cttcaagagg gcgctaaggt atacgctgag cagttcggca tcgaccctga    28800
ggacgttgat tatcagcgtg gtttcaacgg ggacattacc gagcgtaaca tctcgctgta    28860
tggtgcgcat gataacttct tgagccagca agctcagaag ggcgctatca tgaacagccg    28920
agtggaactc aacggtgtcc ttcaagaccc tgatatgctg cgtcgtccag actctgctga    28980
cttctttgag aagtatatcg acaacggtct ggttactggc gcaatcccat ctgatgctca    29040
agccacacag cttataagcc aagcgttcag tgacgcttct agccgtgctg gtggtgctga    29100
```

```
cttcctgatg cgagtcggtg acaagaaggt aacacttaac ggagccacta cgacttaccg    29160
agagttgatt ggtgaggaac agtggaacgc tctcatggtc acagcacaac gttctcagtt    29220
tgagactgac gcgaagctga acgagcagta tcgcttgaag attaactctg cgctgaacca    29280
agaggaccca aggacagctt gggagatgct tcaaggtatc aaggctgaac tagataaggt    29340
ccaacctgat gagcagatga caccacaacg tgagtggcta atctccgcac aggaacaagt    29400
tcagaatcag atgaacgcat ggacgaaagc tcaggccaag gctctggacg attccatgaa    29460
gtcaatgaac aaacttgacg taatcgacaa gcaattccag aagcgaatca acggtgagtg    29520
ggtctcaacg gatttttaagg atatgccagt caacgagaac actggtgagt tcaagcatag    29580
cgatatggtt aactacgcca ataagaagct cgctgagatt gacagtatgg acattccaga    29640
cggtgccaag gatgctatga agttgaagta ccttcaagcg gactctaagg acggagcatt    29700
ccgtacagcc atcggaacca tggtcactga cgctggtcaa gagtggtctg ccgctgtgat    29760
taacggtaag ttaccagaac gaaccccagc tatggatgct ctgcgcagaa tccgcaatgc    29820
tgaccctcag ttgattgctg cgctatacc agaccaagct gagctattcc tgacgatgga    29880
catgatggac aagcagggta ttgaccctca ggttattctt gatgccgacc gactgactgt    29940
taagcggtcc aaagagcaac gctttgagga tgataaagca ttcgagtctg cactgaatgc    30000
atctaaggct cctgagattg cccgtatgcc agcgtcactg cgcgaatctg cacgtaagat    30060
ttatgactcc gttaagtatc gctcggggaa cgaaagcatg gctatggagc agatgaccaa    30120
gttccttaag gaatctacct acacgttcac tggtgatgat gttgacggtg ataccgttgg    30180
tgtgattcct aagaatatga tgcaggttaa ctctgacccg aaatcatggg agcaaggtcg    30240
ggatattctg gaggaagcac gtaagggaat cattgcgagc aacccttgga taaccaataa    30300
gcaactgacc atgtattctc aaggtgactc catttacctt atggacacca caggtcaagt    30360
cagagtccga tacgacaaag agttactctc gaaggtctgg agtgagaacc agaagaaact    30420
cgaagagaaa gctcgtgaga aggctctggc tgatgtgaac aagcgagcac ctatagttgc    30480
cgctacgaag gcccgtgaag ctgctgctaa acgagtccga gagaaacgta acagactcc    30540 taagttcatc tacggacgta aggagtaact aaaggctaca taaggaggcc ctaaatggat    30600
aagtacgata agaacgtacc aagtgattat gatggtctgt tccaaaaggc tgctgatgcc    30660 aacgggtct cttatgacct tttacgtaaa gtcgcttgga cagaatcacg atttgtgcct    30720
acagcaaaat ctaagactgg accattaggc atgatgcaat ttaccaaggc aaccgctaag    30780
gccctcggtc tgcgagttac cgatggtcca gacgacgacc gactgaaccc tgagttagct    30840
attaatgctg ccgctaagca acttgcaggt ctggtaggga gtttgatgg cgatgaactc    30900 aaagctgccc ttgcgtacaa ccaaggcgag ggacgcttgg gtaatccaca acttgaggcg    30960
tactctaagg gagacttcgc atcaatctct gaggagggac gtaactacat gcgtaacctt    31020
ctggatgttg ctaagtcacc tatggctgga cagttggaaa cttttggtgg cataacccca    31080
aagggtaaag gcattccggc tgaggtagga ttggctggaa ttggtcacaa gcagaaagta    31140
acacaggaac ttcctgagtc cacaagtttt gacgttaagg gtatcgaaca ggaggctacg    31200
gcgaaaccat cgccaaggga cttttgggag acccacggaa aaacacttga cgagtacaac    31260
agtcgttcaa ccttcttcgg attcaaaaat gctgccgaag ctgaactctc caactcagtc    31320
gctgggatgg cttttccgtgc tggtcgtctc gataatggtt ttgatgtgtt taaagacacc    31380
attacgccga ctcgctggaa ctctcacatc tggactccag aggagttaga gaagattcga    31440
acagaggtta agaaccctgc gtacatcaac gttgtaactg gtggttcccc tgagaacctc    31500
```

```
gatgacctca ttaaattggc taacgagaac tttgagaatg actcccgcgc tgccgaggct   31560
ggcctaggtg ccaaactgag tgctggtatt attggtgctg gtgtggaccc gcttagctat   31620
gttcctatgg tcggtgtcac tggtaagggc tttaagttaa tcataaggc tcttgtagtt     31680 ggtgccgaaa gtgctgctct gaacgttgca tccgaaggtc tccgtacctc cgtagctggt   31740
ggtgacgcag actatgcggg tgctgcctta ggtggctttg tgtttggcgc aggcatgtct   31800
gcaatcagtg acgctgtagc tgctggactg aaacgcagta accagaagc tgagttcgac    31860 aatgagttca tcggtcctat gatgcgattg gaagcccgtg agacagcacg aaacgccaac   31920
tctgcggacc tctctcggat gaacactgag aacatgaagt ttgaaggtga acataatggt   31980
gtcccttatg aggacttacc aacagagaga ggtgccgtgg tgttacatga tggctccgtt   32040
ctaagtgcaa gcaacccaat caaccctaag actctaaaag agttctccga ggttgaccct   32100
gagaaggctg cgcgaggaat caaactggct gggttcaccg agattggctt gaagaccttg   32160
gggtctgacg atgctgacat ccgtagagtg gctatcgacc tcgttcgctc tcctactggt   32220
atgcagtctg gtgcctcagg taagttcggt gcaacagctt ctgacatcca tgagagactt   32280
catggtactg accagcgtac ttataatgac ttgtacaaag caatgtctga cgctatgaaa   32340
gaccctgagt tctctactgg cggcgctaag atgtcccgtg aagaaactcg atacactatc   32400
taccgtagag cggcactagc tattgagcgt ccagaactac agaaggcact cactccgtct   32460
gagagaatcg ttatggacat cattaagcgt cactttgaca ccaagcgtga acttatggaa   32520
aacccagcaa tattcggtaa cacaaaggct gtgagtatct tccctgagag tcgccacaaa   32580
ggtacttacg ttcctcacgt atatgaccgt catgccaagg cgctgatgat tcaacgctac   32640
ggtgccgaag gtttgcagga agggattgcc cgctcatgga tgaacagcta cgtctccaga   32700
cctgaggtca aggccagagt cgatgagatg cttaaggaat tacacggggt gaaggaagta   32760
acaccagaga tggtagagaa gtacgctatg gataaggctt atggtatctc ccactcagac   32820
cagttcacca acagttccat aatagaagag aacattgagg gcttagtagg tatcgagaat   32880
aactcattcc ttgaggcacg taacttgttt gattcggacc tatccatcac tatgccagac   32940
ggacagcaat tctcagtgaa tgacctaagg gacttcgata tgttccgcat catgccagcg   33000
tatgaccgcc gtgtcaatgg tgacatcgcc atcatgggt ctactggtaa aaccactaag    33060
gaacttaagg atgagatttt ggctctcaaa gcgaaagctg agggagacgg taagaagact   33120
ggcgaggtac atgctttaat ggataccgtt aagattctta ctggtcgtgc tagacgcaat   33180
caggacactg tgtgggaaac ctcactgcgt gccatcaatg acctagggtt cttcgctaag   33240
aacgcctaca tgggtgctca gaacattacg gagattgctg ggatgattgt cactggtaac   33300
gttcgtgctc tagggcatgg tatcccaatt ctgcgtgata cactctacaa gtctaaacca   33360
gtttcagcta aggaactcaa ggaactccat gcgtctctgt tcgggaagga ggtggaccag   33420
ttgattcggc taaacgtgc tgacattgtg cagcgcctaa gggaagcaac tgataccgga   33480
cctgccgtgg cgaacatcgt agggaccttg aagtattcaa cacaggaact ggctgctcgc   33540
tctccgtgga ctaagctact gaacggaacc actaactacc ttctggatgc tgcgcgtcaa   33600
ggtatgcttg gggatgttat tagtgccacc ctaacaggta agactacccg ctgggagaaa   33660
gaaggcttcc ttcgtggtgc ctccgtaact cctgagcaga tggctggcat caagtctctc   33720
atcaaggaac atatggtacg cggtgaggac gggaagttta ccgttaagga caagcaagcg   33780
ttctctatgg acccacgggc tatggactta tggagactgg ctgacaaggt agctgatgag   33840
```

```
gcaatgctgc gtccacataa ggtgtcctta caggattccc atgcgttcgg agcactaggt    33900
aagatggtta tgcagtttaa gtctttcact atcaagtccc ttaactctaa gttcctgcga    33960
accttctatg atggatacaa gaacaaccga gcgattgacg ctgcgctgag catcatcacc    34020
tctatgggtc tcgctggtgg tttctatgct atggctgcac acgtcaaagc atacgctctg    34080
cctaaggaga aacgtaagga gtacttggag cgtgcactgg acccaaccat gattgcccac    34140
gctgcgttat ctcgtagttc tcaattgggt gctccttttgg ctatggttga cctagttggt    34200
```

```
gacagtcgtt cagtacctaa tgcaatcatg gtggagaacg agtaattggt aaatcacaag   36300
gaaagacgtg tagtccacgg atggactctc aaggaggtac aaggtgctat cattagactt   36360
taacaacgaa ttgattaagg ctgctccaat tgttgggacg ggtgtagcag atgttagtgc   36420
tcgactgttc tttgggttaa gccttaacga atggttctac gttgctgcta tcgcctacac   36480
agtggttcag attggtgcca aggtagtcga taagatgatt gactggaaga aagccaataa   36540
ggagtgatat gtatggaaaa ggataagagc cttattacat tcttagagat gttggacact   36600
gcgatggctc agcgtatgct tgcggacctt tcggaccatg agcgtcgctc tccgcaactc   36660
tataatgcta ttaacaaact gttagaccgc cacaagttcc agattggtaa gttgcagccg   36720
gatgttcaca tcttaggtgg ccttgctggt gctcttgaag agtacaaaga gaaagtcggt   36780
gataacggtc ttacggatga tgatatttac acattacagt gatatactca aggccactac   36840
agatagtggt ctttatggat gtcattgtct atacgagatg ctcctacgtg aaatctgaaa   36900
gttaacggga ggcattatgc tagaattttt acgtaagcta atcccttggg ttctcgctgg   36960
gatgctattc gggttaggat ggcatctagg gtcagactca atggacgcta atggaaaca   37020 ggaggtacac aatgagtacg ttaagagagt tgaggctgcg aagagcactc aaagagcaat   37080
cgatgcggta tctgctaagt atcaagaaga ccttgccgcg ctggaaggga gcactgatag   37140
gattatttct gatttgcgta gcgacaataa gcggttgcgc gtcagagtca aaactaccgg   37200
aacctccgat ggtcagtgtg gattcgagcc tgatggtcga gccgaacttg acgaccgaga   37260
tgctaaacgt attctcgcag tgacccagaa gggtgacgca tggattcgtg cgttacagga   37320
tactattcgt gaactgcaac gtaagtagga aatcaagtaa ggaggcaatg tgtctactca   37380
atccaatcgt aatgcgctcg tagtggcgca actgaaagga gacttcgtgg cgttcctatt   37440
cgtcttatgg aaggcgctaa acctaccggt gcccactaag tgtcagattg acatggctaa   37500
ggtgctggcg aatggagaca acaagaagtt catcttacag gctttccgtg gtatcggtaa   37560
gtcgttcatc acatgtgcgt tcgttgtgtg gtccttatgg agagaccctc agttgaagat   37620
acttatcgta tcagcctcta aggagcgtgc agacgctaac tccatctttta ttaagaacat   37680 cattgacctg ctgccattcc tatctgagtt aaagccaaga cccggacagc gtgactcggt   37740
aatcagcttt gatgtaggcc cagccaatcc tgaccactct cctagtgtga aatcagtagg   37800
tatcactggt cagttaactg gtagccgtgc tgacattatc attgcggatg acgttgagat   37860
tccgtctaac agcgcaacta tgggtgcccg tgagaagcta tggactctgg ttcaggagtt   37920
cgctgcgtta cttaaaccgc tgccttcctc tcgcgttatc taccttggta cacctcagac   37980
agagatgact ctctataagg aacttgagga taaccgtggg tacacaacca ttatctggcc   38040
tgctctgtac ccaaggacac gtgaagagaa cctctattac tcacagcgtc ttgctcctat   38100
gttacgcgct gagtacgatg agaaccctga ggcacttgct gggactccaa cagacccagt   38160
gcgctttgac cgtgatgacc tgcgcgacg tgagttggaa tacggtaagg ctggctttac   38220
gctacagttc atgcttaacc ctaaccttag tgatgccgag aagtacccgc tgaggcttcg   38280
tgacgctatc gtagcggcct tagacttaga gaaggcccca atgcattacc agtggcttcc   38340
gaaccgtcag aacatcattg aggaccttcc taacgttggc cttaagggtg atgacctgca   38400
tacgtaccac gattgttcca acaactcagg tcagtaccaa cagaagattc tggtcattga   38460
ccctagtggt cgcggtaagg acgaaacagg ttacgctgtg ctgtacacac tgaacggtta   38520
catctacctt atggaagctg gaggttccg tgatggctac tccgataaga ccccttgagtt   38580
```

```
actcgctaag aaggcaaagc aatggggagt ccagacggtt gtctacgaga gtaacttcgg   38640
tgacggtatg ttcggtaagg tattcagtcc tatccttctt aaacaccaca actgtgcgat   38700
ggaagagatt cgtgcccgtg gtatgaaaga gatgcgtatt tgcgataccc ttgagccagt   38760
catgcagact caccgccttg taattcgtga tgaggtcatt agggccgact accagtccgc   38820
tcgtgacgta gacggtaagc atgacgttaa gtactcgttg ttctaccaga tgacccgtat   38880
cactcgtgag aaaggcgctc tggctcatga tgaccgattg gatgcccttg cgttaggcat   38940
tgagtatctc cgtgagtcca tgcagttgga ttccgttaag gtcgagggtg aagtacttgc   39000
tgacttcctt gaggaacaca tgatgcgtcc tacggttgct gctacgcata tcattgagat   39060
gtctgtggga ggagttgatg tgtactctga ggacgatgag ggttacggta cgtctttcat   39120
tgagtggtga tttatgcatt aggactgcat agggatgcac tatagaccac ggatggtcag   39180
ttctttaagt tactgaaaag acacgataaa ttaatacgac tcactatagg gagaggaggg   39240
acgaaaggtt actatataga tactgaatga atacttatag agtgcataaa gtatgcataa   39300
tggtgtacct agagtgacct ctaagaatgg tgattatatt gtattagtat caccttaact   39360
taaggaccaa cataaaggga ggagactcat gttccgctta ttgttgaacc tactgcggca   39420
tagagtcacc taccgatttc ttgtggtact ttgtgctgcc cttgggtacg catctcttac   39480
tggagacctc agttcactgg agtctgtcgt ttgctctata ctcacttgta gcgattaggg   39540
tcttcctgac cgactgatgg ctcaccgagg gattcagcgg tatgattgca tcacaccact   39600
tcatccctat agagtcaagt cctaaggtat acccataaag agcctctaat ggtctatcct   39660
aaggtctata cctaaagata ggccatccta tcagtgtcac ctaaagaggg tcttagagag   39720
ggcctatgga gttcctatag ggtccttaa aatataccat aaaaatctga gtgactatct   39780
cacagtgtac ggacctaaag ttcccccata gggggtacct aaagcccagc caatcaccta   39840
aagtcaacct tcggttgacc ttgagggttc cctaagggtt ggggatgacc cttgggtttg   39900
tctttgggtg ttaccttgag tgtctctctg tgtccct                             39937
```

ONCOLYTIC T7 BACTERIOPHAGE HAVING CYTOKINE GENE AND DISPLAYING HOMING PEPTIDE ON CAPSID AND ITS USE FOR TREATING MELANOMA

STATEMENT OF GOVERNMENT SUPPORT

The invention was made with government support under grants number 2017M3A9B8069292 and 2019R1F1A1058057 awarded by National Research Foundation, Republic of Korea.

CROSS-REFERENCE TO RELATED APPLICATIONS

This application claims the benefit of Korean Patent Application NO. 2019-0081977 filed Jul. 8, 2019 in the Korean Intellectual Property Office, disclosure of which is incorporated herein by reference.

SEQUENCE LISTING

The Sequence Listing submitted in text format (.txt) filed on Nov. 30, 2021, named "SequenceListing.txt", created on Nov. 30, 2021, (52.3 KB), is incorporated herein by reference.

BACKGROUND OF THE INVENTION

Field of the Invention

The technical field of the present disclosure relates to oncolytic recombinant bacteriophage and its use for treating cancer.

Description of the Related Art

Oncolytic Virus (OV) is a virus that infects and lysis cancer cells [A. Reale, et al. Perspectives on immunotherapy via oncolytic viruses, Infect. Agent. Cancer 14 (2019) 1-8]. OV infects actively proliferating cancer cells and lyses the cancer cells by propagating inside the cells. In addition to lysis by the virus, tumors are also attacked by the immune system due to the presence of immunogenic viruses. Currently, HSV-1-based oncolytic virus (T-VEC) is approved by the FDA and is currently in clinical use. [I. Puzanov, et al. Talimogene laherparepvec in combination with ipilimumab in previously untreated, unresectable stage IIIB-IV melanoma. J. Clin. Oncology 34 (2016) 2619-2626]. Virus that infects humans but attenuated and is tested as OV includes adenoviruses, leukemia viruses, measles viruses, mumps viruses, and influenza viruses and the like. [S. Tayeb, et al. Therapeutic potential of oncolytic Newcastle disease virus: a critical review. Oncolytic Virother. 4 (2015) 49-62].

However, OV is often not effective enough to treat solid tumors, and safety and efficacy do not always coincide [A. Reale, et al. ibid]. Oncolytic virus is known to exhibit a certain range of toxicity [A. Reale, et al. ibid]. In addition, live viruses can also cause a problem because they can be transmitted from the primary caregiver to the health care worker and the people at home through the contact [E. V. Robilotti, et al. Viral oncolytic immunotherapy in the war on cancer: Infection control considerations, Infect. Control Hosp. Epidemiol. 40 (2019) 350-354].

Bacteriophages, on the other hand, naturally infect bacteria and are safer than viruses, especially in human infection problems. Bacteriophage T4 and similar type HAP1 have been reported to inhibit lung metastasis in mouse models [K. Dabrowska, et al., Antitumor activity of bacteriophages in murine experimental cancer models caused possibly by inhibition of beta3 integrin signaling pathway. Acta Virol. 48 (2004) 241-248]. Eriksson et al reported that M13 phages displaying Fab fragment of antibody on their surface can decrease the rate of tumor growth and increase the survival rate of the mouse when the phage was injected into the tumor bearing mice [F. Eriksson, W. D. et al., Tumor specific phage particles promote tumor regression in a mouse melanoma model. Cancer Immunol. Immunother. 56 (2007) 677-687].

SUMMARY OF THE INVENTION

Phage T7 has a genome size of 40 kbp, which is much smaller than T4 phages of 168 kbp making them easy to be manipulated. The fast growth rate of T7 phage provide further advantages in preparing the phage at high concentrations in short time. However there are no reports of the development of oncolytic phage based on T7. There are needs to develop various oncolytic phages based on T7 phage.

In one aspect, there is provided an oncolytic recombinant bacteriophage T7 displaying on its capsid tumor specific homing peptide and comprising cytokine gene in the genome for expression in mammalian eukaryotic cell.

In the foregoing phage, the cytokine gene which can be incorporated into the genome of the phage is the one that can inhibit the tumor growth or induce apoptosis of the tumor cell is IL (Interleukin)-1α, TNF (Tumor Necrosis Factor)-α or GM-CSF (Granulocyte-Macrophage Colony-Stimulating Factor). The amino acid sequence and the nucleic acid sequence encoding the same is known in the art and can be from various species such as mouse, and human beings and the like.

In the foregoing phage, the tumor the present phage is targeting includes, but is not limited to, melanoma, lung cancer, prostate cancer, glioblastoma, pancreatic cancer, leukemia, or breast cancer.

In one embodiment, the amino acid sequence of tumor specific homing peptide is CTVALPGGYVRVC for melanoma represented by SEQ ID NO: 1.

In other embodiments, the amino acid sequence of tumor specific homing peptide is a cyclic RGD-$\{_D$-F$\}$-$\{$N-methyl-Val$\}$ for lung cancer and glioblastoma represented by SEQ ID NO: 2.

In still other embodiments, the amino acid sequence of tumor specific homing peptide is RTDLXXL for pancreatic cancer represented by SEQ ID NO: 3.

In still other embodiments, the amino acid sequence of tumor specific homing peptide is cyclic RGD-$\{_D$-F$\}$-$\{$N-methyl-Val$\}$ or WQPDTAHHWATL for prostate cancer represented by SEQ ID NO: 2 and 4, respectively.

In still other embodiments, the amino acid sequence of tumor specific homing peptide is HAIYPRH for leukemia represented by SEQ ID NO: 5.

In still other embodiments, the amino acid sequence of tumor specific homing peptide is YSAYPDSVPMMS for breast cancer represented by SEQ ID NO: 6.

In the present disclosure, amino acids are denoted by single letter code defined in the related art as follows: A, Alanine; R, Arginine; N, Asparagine; D, Aspartic acid; C, Cysteine; E, Glutamic acid; Q, Glutamine; G, Glycine; H, Histidine; I, Isoleucine; L, Leucine; K, Lysine; M, Methionine; F, Phenylalanine; P, Proline; S, Serine; T, Threonine;

W, Tryptophan; Y, Tyrosine; V, Valine; Z, Glutamic acid and Glutamine; X, any amino acid in Sequence listing.

In the foregoing phage, the cytokine gene is integrated into a Pac I restriction site (5'-TTAAT^TA-3') located 27223 bp-27230 bp of the T7 genome based on the sequence disclosed as GenBank accession number V01146.1 (SEQ ID NO: 10).

In the foregoing phage, the cytokine gene encodes GM-CSF, and the homing peptide is specific for melanoma and is represented by SEQ ID NO: 1.

In other aspect, there is provided a composition comprising the oncolytic recombinant bacteriophage T7 disclosed herein.

In the foregoing composition, it is provided as a pharmaceutical composition.

In the foregoing composition, it is used to treat cancer, in which the type of caner may be determined by the type of homing peptide displayed on the capsid.

Advantageous Effect

The oncolytic recombinant bacteriophage T7 of the present disclosure expresses cytokine in mammalian eukaryotic cells when delivered to the target tumor cells by binding to the cells through the homing peptide. Further the present peptide can effectively induce immune response to the phage leading to an effective cancer therapy. The bacteriophage as a pathogen for bacteria not human beings provides further advantages in the manipulation of the genes and the production of recombinant phage for the development of anti-cancer agent.

In one embodiment of the present disclosure, the mouse administered with the present phage was alive until the end of the experiment for at least 25 days. In contrast, just 40% of the mouse untreated survived at the end of the experiment. Further, the size of the tumor of the mouse untreated has increased by 400%, in comparison to 12% increase in the mouse treated for 10 days with the present phage. Further the serum concentration of cytokines IL-1α, TNF-α and GM-CSF was increased. Also the infiltration of macrophages, dendritic cells, CD8 positive T cells, and Natural killer cells to the tumor was observed. The above results indicate that the present oncolytic recombinant bacteriophage T7 is able to change the microenvironment of tumor and recruit immune cells having anti-cancer activities and thus can effectively inhibit the growth tumor cells.

DETAILED DESCRIPTION OF THE EMBODIMENTS

Figure 1:
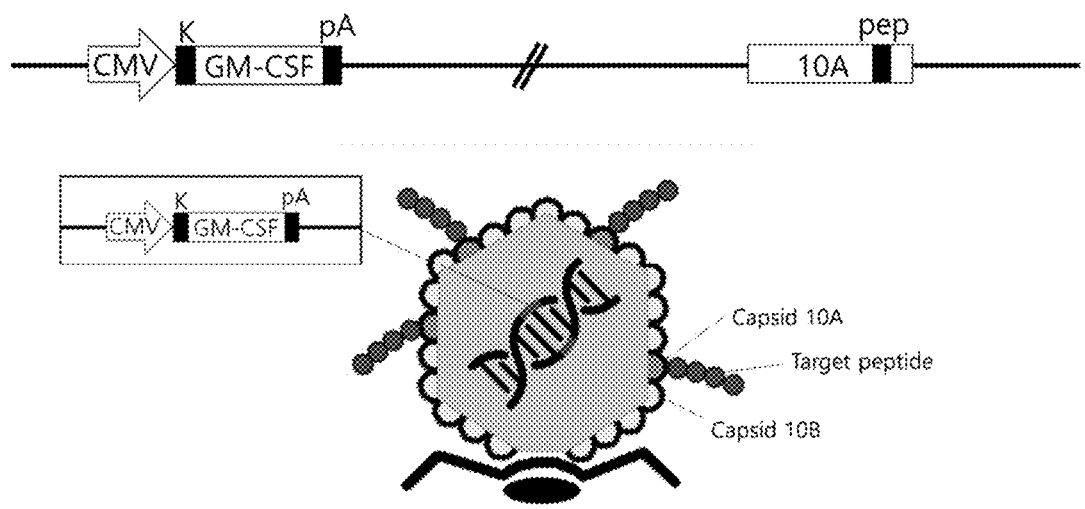
FIG. 1 is a schematic diagram of the recombinant T7 constructed herein engineered to display homing peptide targeting particular cancer cells and to express in cancer cells cytokine GM-CSF having anticancer effect.

The present disclosure is based, in part, on the discovery that the recombinant bacteriophage T7 can be effectively used as anticancer agents. The bacteriophage, a natural pathogen specific for bacteria can be advantageously used for the development of anticancer agent providing particular advantages in the gene manipulation and production thereof.

In one aspect of the present disclosure, there is provided an oncolytic recombinant bacteriophage T7 displaying on its capsid a tumor specific homing peptide and comprising a cytokine gene in its genome for expression in mammalian eukaryotic cells.

The recombinant bacteriophage T7 according to one embodiment of the present disclosure is able to target a particular tumor by specifically binding to the tumor cells due to the presence of homing peptides displayed on its capsid, when the phage is administered, for example by intravenous injection. After the attachment to the particular tumor cells, the present phage enters the cells by receptor-mediated endocytosis and the phage DNA migrates into the nucleus to express cytokine from the gene integrated into the genome, for example, from the GM-CSF cassette and to produce cytokines in the cancer cells.

T7 phages are phages that infect rough *E. coli* without full-length 0-antigen polysaccharides on its surface and other enteric bacteria, that lack full-length 0-antigen polysaccharides on their surface. The T7 phage has dsDNA genome of 40 kbp in length with capsids surrounding the genome and a tail structure attached to the capsid and the full sequence of the genome has been identified (Dunn, J. J.; Studier, F. W. (1983). "Complete nucleotide sequence of bacteriophage T7 DNA and the locations of T7 genetic elements". Journal of Molecular Biology. 166 (4): 477-535. doi:10.1016/S0022-2836(83)80282-4. PMID 6864790). In one embodiment of the present disclosure, the sequence of a wild type T7 phage used as a parent in the present disclosure can be found as GenBank accession number V01146.1 (SEQ ID NO: 10). (website www dot ncbi. nlm.nih.gov/nuccoreN01146.1). The information and the sequence of T7 phages are also available from Bacteriophage Bank of Korea (website www dot phagebank.or.kr/).

The recombinant bacteriophage T7 according to one embodiment of the present disclosure is modified to display homing peptide on its capsid. Bacteriophage T7 capsid is consisted of proteins 10A and 10B. In the present disclosure, the homing peptide is expressed as a fusion to the C-terminus of protein 10B for displaying at the outside capsid.

The recombinant bacteriophage T7 according to one embodiment of the present disclosure is modified to have a cytokine gene that can be expressed in mammalian eukaryotic cells. Such cytokine genes are not particularly limited as long as they are able to induce or help induce apoptosis of cancer cells, and include, for example, proinflammatory cytokines such as IL(Interleukin)-1α, TNF(Tumor necrosis factor)-α or GM-CSF (Granulocyte-macrophage colony-stimulating factor) and the like. The amino acid sequences of various cytokines and the DNA sequence encoding the same is known in the art and available from the public data base. In one embodiment of the present disclosure, the cytokine employed is GM-CSF, the mouse sequence of which is known as Gene ID: 12981 for the gene and NP_034099.2 for the protein.

The gene encoding the GM-CSF is provided as part of a expression cassette, in which the gene coding for GM-CSF is under the control of a eukaryotic promoter. The structures and arrangement of such cassettes including cytokine gene can be constructed without difficulties by one of ordinary skill in the art in view of the present disclosure. In one embodiment, the cytokine expression cassette is inserted at PacI restriction site of 27223 bp-27230 bp of T7 bacteriophage genome, the sequence of which is disclosed and available from the public domain as GenBank accession number V01146.1 (SEQ ID NO: 10). It was found in the present disclosure that the site to which the present cassette is inserted does not affect the yield of the present recombinant T7 phage production.

The recombinant T7 bacteriophage according to the present disclosure displays on its capsid homing peptide that specifically recognize a particular tumor or tumor tissue, and have a cytokine gene inserted in the genome in a way to be expressed in eukaryotic cells.

Homing peptides are referred to as a peptide that specifically bind to the vasculature of a particular tumor tissue such as Lung cancer, Prostate Cancer, Breast Cancer, Melanoma, and Colorectal Cancer and the like via receptor. Some of the peptides include RGD (Arg-Gly-Asp) or NGR (Asn-Gly-Arg) as a common motif. Various homing peptides that specifically recognize tumor tissue are known in the art. For example, tumor specific homing peptides are available from website www dot webs.iiitd.edu.in/raghava/tumorhope/. The present recombinant bacteriophage T7 can display various homing peptide depending on the type of tumor to be targeted and/or treated. One of ordinary skill in the would be able to select a proper homing peptide in consideration of the factors such as the characteristics of a tumor at issue.

In one embodiment, the tumor, tumor cells or tumor tissues to be targeted by the present bacteriophage T7 include, but is not limited to, melanoma, lung cancer, prostate cancer, glioblastoma, pancreatic cancer, leukemia, and breast cancer.

In other embodiment, the homing peptide specific for the cancer include, but is not limited to, for example: CTVALPGGYVRVC (SEQ ID NO: 1) for melanoma, cyclic RGD-{$_D$-F}-{N-methyl-Val} (SEQ ID NO: 2) for lung cancer and glioblastoma, RTDLXXL(SEQ ID NO: 3) for pancreatic cancer, cyclic RGD-{$_D$-F}-{N-methyl-Val} (SEQ ID NO: 2) or WQPDTAHHWATL(SEQ ID NO: 4) for prostate cancer; HAIYPRH(SEQ ID NO: 5) for leukemia and YSAYPDSVPMMS(SEQ ID NO: 6) for breast cancer. The peptide of SEQ ID NO: 2 has a circular structure in which a peptide bond is formed between R and V.

In one embodiment, pep42 [CTVALPGGYVRVC](SEQ ID NO: 1) targeting grp78 specific for melanoma is employed in the present disclosure.

The recombinant T7 bacteriophage of the present disclosure can induce a direct lysis of tumor cells and immune response to the phage thus leading to the anticancer effect. The bacteriophage, a natural pathogen for bacteria, not for human beings, employed herein is particularly advantageous in the manipulation of the genes and the production of the phage.

In other aspect, the present disclosure relates to composition for treating cancer comprising the recombinant oncolytic T7 bacteriophage as disclosed herein.

In one embodiment, the present composition is provided as a pharmaceutical composition, which comprises a pharmaceutically acceptable excipients or carriers, The type of cancer which can be treated by the present composition can be determined depending on the capsid displayed by the present phage.

In one embodiment, the composition comprises the phage which displays on its capsid CTVALPGGYVRVC(SEQ ID NO: 1) for melanoma, cyclic RGD-$\{_D$-F$\}$-$\{$N-methyl-Val$\}$ (SEQ ID NO: 2) for lung cancer and glioblastoma, RTDLXXL(SEQ ID NO: 3) for pancreatic cancer, cyclic RGD-$\{_D$-F$\}$-$\{$N-methyl-Val$\}$ (SEQ ID NO: 2) or WQPD-TAHHWATL(SEQ ID NO: 4) for prostate cancer; HAIY-PRH(SEQ ID NO: 5) for leukemia and YSAYPDSVPMMS (SEQ ID NO: 6) for breast cancer.

As used herein, the term "treatment" means any action that ameliorates or beneficially alters the disease by the administration of the present composition. Those skilled in the art will be able to determine the extent to which the disease is improved or treated, with reference to the knowledge known in the art.

The composition may further comprise excipients such as suitable carriers, diluents, preservatives, stabilizers, wetting agents, emulsifiers, solubilizers, sweeteners, colorants, osmotic pressure-controlling agents, antioxidants and the like commonly used in the preparation of the compositions. Specifically, lactose, dextrose, sucrose, sorbitol, mannitol xylitol, erythritol, maltitol, starch, acacia rubber, alginate, gelatin, calcium phosphate, calcium silicate, cellulose, methylcellulose, microcrystalline cellulose, polyvinylpyrrolidone, water, methyl hydroxy benzoate, propyl hydroxy benzoate, talc, magnesium, stearate, mineral oil, and the like may be employed.

The present composition can be administered to mammals including human beings through various route and the route of administration of the present composition can be selected easily for example according to the formulation of the composition. For example, it may be formulated in the form of a sterile injectable solution and the like and administered locally or systemically, particularly parenteral administration is preferred.

Formulations for parenteral administration include sterile aqueous solutions, non-aqueous solvents, suspensions, emulsions, lyophilized preparations, suppositories. As the non-aqueous solvent and the suspension solvent, propylene glycol, polyethylene glycol, vegetable oil such as olive oil, injectable ester such as ethyl oleate, and the like can be used.

Furthermore, the pharmaceutical compositions according to the present invention are preferably formulated using appropriate methods known in the art or using methods disclosed in Remington's Pharmaceutical Science (Latest Edition, Mack Publishing Company, Easton Pa.).

The dosage of the composition according to the present disclosure may vary depending on various condition such as the weight, age, sex, health condition, diet, time of administration, route of administration, excretion rate, and severity of the disease. It is apparent to one skilled in the art that the dosage can be added or subtracted as needed and can be determined depending on the patient condition and the like in view of the knowledge known in the art. The present composition can be administered once a day or divided into several times within the desired range, the administration period is not particularly limited.

The present disclosure is further explained in more detail with reference to the following examples. These examples, however, should not be interpreted as limiting the scope of the present invention in any manner.

EXAMPLE

Method and Materials

Construction and Production of Recombinant T7 Bacteriophage

The homing peptide used was pep42 [CTVALPG-GYVRVC] (SEQ ID NO: 1) targeting grp78 on cancer cells. Both strands of oligonucleotides encoding the peptide were synthesized (Bioneer, Korea) and annealed and ligated between EcoRI and HindIII sites in multiple cloning sites of T7 Select® 10-3 cloning kits (Novagen, Canada). The resulting T7 Select vector was used for electroporation into *Escherichia coli* BLT5403 (Novagen, Canada) to produce homing peptide-displaying phages. Additionally, a cassette expressing GM-CSF under CMV promoter was synthesized (Bioneer, Korea) and used to clone into the above described T7 genomic DNA (GenBank accession number V01146.1, SEQ ID NO: 10) digested with the restriction enzyme PacI at 27,225 base pair. The synthesized cassette consisted of CMV promoter, KOZAK sequence, the ORF encoding murine GM-CSF (Gene ID 12981), and BGH polyA signal.

The recombinant phage was used to infect freshly cultured *E. coli* BLT5403 in a 500 ml culture media at the multiplicity of infection (MOI) of 0.1. The mixture was incubated at room temperature for phage adsorption for one hour followed by shaking incubation at 37° C. for 3 hours. Chloroform was added to the culture at a final concentration of 5% (v/v) for complete lysis of bacteria and the culture was then shaking incubated for 15 more minutes. NaCl was subsequently added at a final concentration of 6% (weight/volume) and the culture was incubated at 4° C. for 1 hour. To remove any remaining bacterial cells or debris, the mixture was subjected to centrifugation at 11,000×g for 10 minutes. The supernatant was recovered and PEG8000 was added at a final concentration of 10% (weight/volume). The mixture was again subjected to centrifugation at 11,000×g for 10 minutes. Supernatant was discarded and the pellet was resuspended in 1 ml of SM buffer (50 mM Tris-HCl pH7.5, 100 mM NaCl, 8 mM MgSO4). 1 ml of chloroform was added and the mixture was rigorously vortexed and subjected to a centrifugation at 2,000×g for 15 minutes. The upper phase was recovered and subjected to an ultracentrifugation. 3 ml of 40% glycerol was poured into an empty tube followed by the slow addition of 5% glycerol. The upper phase containing phages was then added to the tube and the remaining space was filled with SM buffer. The tube was centrifuged at 270,000×g for one hour. Supernatant was discarded and the pellet containing phages was recovered by resuspension in 1 ml of SM buffer.

Removal of Endotoxins

TRITON X®-114 was added to the phage sample at a final concentration of 1% (v/v) and the mixture was rigorously vortexed. After incubation on ice for 5 minutes, the mixture was rigorously vortexed and subjected to centrifugation at 15,000×g, 37° C. for 1 minute. The upper phase was recovered and used for phage experiments in vitro and in vivo.

Cancer Cell Line and Culture Conditions

The B16F10 mouse melanoma cell line (KCLB80008) was obtained from the Korean Cell Line Bank at Seoul National University. Cells were grown in Dulbecco's modified Eagle's medium (DMEM, Thermo Fisher Scientific, USA) supplemented with fetal bovine serum (FBS, CELLect, USA) at a final concentration of 10% (v/v) and penicillin/streptomycin (Sigma Aldrich, USA) at a final concentration of 1% (v/v).

Confocal Microscopy Analysis of Phage Transduction

For staining bacteriophage T7 after transduction, $1\times10^5$ B16F10 cells were seeded in a 6 well plate with coverslip and grown in a CO2 incubator. Media was discarded after 24 hours and $1\times10^7$ PFU of phages in SM buffer were added to each well and incubated for 30 minutes. Unbound phages were washed out and the cells were fixed with cold acetone. Blocking solution (1% bovine serum albumin in PBS) was added and the mixture was incubated for 30 minutes. Cells were then treated with 1:500 diluted anti-T7 tag antibody (ab9138, Abcam, USA) for one hour followed by washing with PBS three times. Secondary antibody (1:1000 diluted anti-goat antibody, ab6881 Abcam, USA) was added and the mixture was incubated for one hour followed by washing with PBS three times. The nucleus was stained with 4', 6-diamidino-2-phenylindole (DAPI) for 5 minutes. A laser confocal microscope (LSM 700, Carl Zeiss, Germany) was used for observations. For masking the receptor grp78 prior to phage transduction, 1:100 diluted anti-grp78 antibody (ab21685, Abcam) was added to the cell culture and incubated for 1 hour followed by washing with PBS. Visualization was performed by adding an Alexa®594-labeled secondary antibody (anti-grp78 rabbit antibody, ab150064, Abcam). For the labeling of phage DNA, BrdU (Thermo Fisher Scientific, USA) was added at a final concentration of 30004 at the time of phage infection to the bacterial culture and the resulting progeny phages were collected.

Cytotoxicity Assay In Vitro $3\times10^4$ B16F10 cells were seeded in a 96 well plate and incubated overnight. Bacteriophages were added to the well at multiplicities of infection (MOI) of 10 or 100 and the mixture was incubated for 24 hours followed by 3-(4,5-dimethylthiazol-2-yl)-2,5-diphenyltetrazolium bromide (MTT) assay (Cell Viability Assay Kit, Dong-In LS, Korea) in accordance with the manufacturer's instructions.

Expression of GM-CSF from Transduced Phage In Vitro $1\times10^6$ B16F10 cells were seeded in a 6 well plate and incubated overnight. Engineered bacteriophage T7 displaying homing peptide (pep42) and expressing GM-CSF was added to the culture at a MOI of 100 and cells were incubated for 3 days. Cells were harvested and lysed with cell extraction buffer (50 mM Tris-HCl, pH8.0, 150 mM NaCl, 0.1% TRITON X®-100, 0.5% sodium dodecyl sulphate, 1 mM sodium orthovanadate, 1 mM NaF) and the lysate was subjected to an SDS-PAGE analysis. Expression was confirmed using the anti-GM-CSF antibody (ab9741, Abcam, USA) and the anti-rabbit secondary antibody (ab6717, Abcam, USA) in a western blot analysis. The same lysate was used for the extraction of total RNA using the TRLEasy® Total RNA Ultrapurification kit (RBC, Taiwan). 5 μg of total RNA was mixed with oligo (dT)18 primer and 1,000 U of reverse transcriptase (DyneBio, Korea). The mixture was annealed at 42° C. for 5 minutes followed by incubation at 50° C. for 60 minutes to allow for enzyme reaction. The reaction was then stopped by incubation at 70° C. for 15 minutes. Realtime PCR was performed with the resulting cDNA, primer, and SYBR Green® qPCR 2X PreMix (DyneBio, Korea). The primer sequence used was forward: 5'GGCCTTGGAAGCATGTAGAG3' (SEQ ID NO: 8), reverse: 5'CCGTAGACCCTGCTCGAATA3' (SEQ ID NO: 9).

Animal Experiments

All animal studies were approved by, and complied with, the regulations and guidelines of the Ethical Committee for Animal Experiments of Hankuk University of Foreign Studies (approval number HUFS-2017-0002). 6-week-old female Balb/C mice were obtained for the experiments (Young Bio, Korea). For tumor size measurement, 30 mice were divided into 6 groups. In vitro cultured $5\times10^6$ B16F10 cells were subcutaneously injected into the right flank of each mouse. Tumor mass was allowed to grow for 1 week until its diameter reached ca. 5 mm. Treatment started one week post melanoma cell graft. Group 1 contained control mice with SM buffer treatment. Group 2 mice were treated with $1\times10^9$ PFU of wild type bacteriophage T7 every day for 10 days. Group 3 mice were treated with $1\times10^9$ PFU of pep42-displaying bacteriophage T7 every day for 10 days. Group 4 mice were treated with $1\times10^9$ PFU of pep42-displaying bacteriophage T7 harboring expression cassette of GM-CSF every day for 10 days. Group 5 mice were treated with $1\times10^9$ PFU of pep42-displaying bacteriophage T7 and 1 ng of GM-CSF (catalogue number Z03300, GenScript, USA) every day for 10 days. Group 6 mice were treated with 1 ng of GM-CSF every day for 10 days. All treatments were injected intravenously (IV) in the tail vein. Tumor volume was measured during the treatment period. After 10 days of treatment, the mice were sacrificed and tumor mass was removed for immunohistological analysis. For serum cytokine analysis, 400 μl of orbital blood collection was performed for each mouse. For survival observations, 30 mice were divided into 6 groups as above and survival was monitored for 25 days. When tumor mass exceeded 10% of total body weight, the mouse was euthanized. The survival graph was plotted in accordance with Kaplan-Meier plot and drawn with Prism GraphPad Software.

In Vivo Imaging $1\times10^9$ PFU of pep42-displaying bacteriophage T7 or wild type bacteriophage T7 was fluorescently labeled with 0.25 mg/ml of fluorochrome-hydroxyl-succinate ester (cy5.5) in a dark room at room temperature for one hour. Cy5.5-labeled phages were injected in tail veins of Balb/C mice bearing B16F10 grafted tumor mass and in vivo live imaging was performed using an FMT 2500™-LX imager (Institute Pasteur Korea) after two hours.

Cytokine ELISA

Serum was obtained from mouse blood by centrifugation at 1000×g for 15 minutes. Mouse cytokines IL-1α, TNF-α, and GM-CSF were measured using Multi-Analite ELISArray® Kits (Qiagen, Germany) in accordance with the manufacturer's instruction. The assay was performed in triplicate.

Immunohistological Analysis

Tumor-bearing mice treated with various phages and/or cytokine were sacrificed and tumor masses were removed. These were then fixed in 10% formalin and haematoxylin-eosin (HE) staining and immunohistochemistry (IHC) were performed (LogOne Bio Convergence Research Foundation, Seoul, Korea).

Transwell Migration Assay 12 mm transwell with 3.0 μm pore (corning transwell polyester membrane cell culture inserts, CLS3462) was used. $1\times10^5$ B16F10 cells were seeded in the lower chamber and incubated at 37° C. for 24 hours. 1×10⁷ PFU of phage T7 displaying pep42 harboring expression cassette of GM-CSF was added to the confluently grown cells and incubated for 24 hours. Then, 1×10⁵ Raw 264.7 cells were loaded in the upper chamber and incubated at 37° C. for 2, 6, or 24 hours. Media were discarded and migrated cells on membrane surfaces were fixed with 1 ml of 70% ethanol at room temperature for 5 minutes followed by drying for 15 minutes. Fixed cells were stained with 0.2% crystal violet at room temperature for 5 minutes followed by washing with distilled water three times. Cells were then observed under a light microscope.

Statistical Analysis

All experiments were performed in triplicate and statistical significance was obtained using one way ANOVA followed by Tukey's test (Prism GraphPad Software). $p<0.05$ was considered as statistically significant.

Example 1. Construction and Preparation of Recombinant T7 Bacteriophage

The homing peptide used was pep42 [CTVALPG-GYVRVC] (SEQ ID NO: 1) targeting grp78 on cancer cells. Both strands of oligonucleotides encoding the peptide were synthesized (Bioneer, Korea) and annealed and ligated between EcoRI and HindIII sites in multiple cloning sites of T7 Select® 10-3 cloning kits (Novagen, Canada). The resulting T7 Select vector was used for electroporation into *Escherichia coli* BLT5403 (Novagen, Canada) to produce homing peptide-displaying phages. The fusion of homing peptide-10B protein integrates into phage capsid. Additionally, a cassette expressing GM-CSF under CMV promoter was synthesized (Bioneer, Korea) and used to clone into the above described T7 genomic DNA (GenBank accession number V01146.1, SEQ ID NO: 10) digested with the restriction enzyme PacI at 27,225 base pair. The synthesized cassette consisted of CMV promoter, KOZAK sequence GCCRCCATGG (R, purine; A or G)(SEQ ID NO: 7), the ORF encoding murine GM-CSF (Gene ID 12981), and BGH polyA signal as shown in FIG. 1.

The recombinant phage was used to infect freshly cultured *E. coli* BLT5403 in a 500 ml culture media at the multiplicity of infection (MOI) of 0.1. The mixture was incubated at room temperature for phage adsorption for one hour followed by shaking incubation at 37° C. for 3 hours. Chloroform was added to the culture at a final concentration of 5% (v/v) for complete lysis of bacteria and the culture was then shaking incubated for 15 more minutes. NaCl was subsequently added at a final concentration of 6% (weight/volume) and the culture was incubated at 4° C. for 1 hour. To remove any remaining bacterial cells or debris, the mixture was subjected to centrifugation at 11,000×g for 10 minutes. The supernatant was recovered and PEG8000 was added at a final concentration of 10% (weight/volume). The mixture was again subjected to centrifugation at 11,000×g for 10 minutes. Supernatant was discarded and the pellet was resuspended in 1 ml of SM buffer (50 mM Tris-HCl pH7.5, 100 mM NaCl, 8 mM MgSO4). 1 ml of chloroform was added and the mixture was rigorously vortexed and subjected to a centrifugation at 2,000×g for 15 minutes. The upper phase was recovered and subjected to an ultracentrifugation. 3 ml of 40% glycerol was poured into an empty tube followed by the slow addition of 5% glycerol. The upper phase containing phages was then added to the tube and the remaining space was filled with SM buffer. The tube was centrifuged at 270,000×g for one hour. Supernatant was discarded and the pellet containing phages was recovered by resuspension in 1 ml of SM buffer.

Endotoxins were removed as below. TRITON X®-114 was added to the phage sample at a final concentration of 1% (v/v) and the mixture was rigorously vortexed. After incubation on ice for 5 minutes, the mixture was rigorously vortexed and subjected to centrifugation at 15,000×g, 37° C. for 1 minute. The upper phase was recovered and used for phage experiments in vitro and in vivo.

Example 2. Characterization of the Present Bacteriophage T7

The engineered bacteriophage T7 displaying homing peptide (pep42) and harboring a mammalian expression cassette of murine GM-CSF was produced and detoxified by removing endotoxins as Example 1 and the toxicity was tested in vitro.

Figure 2:
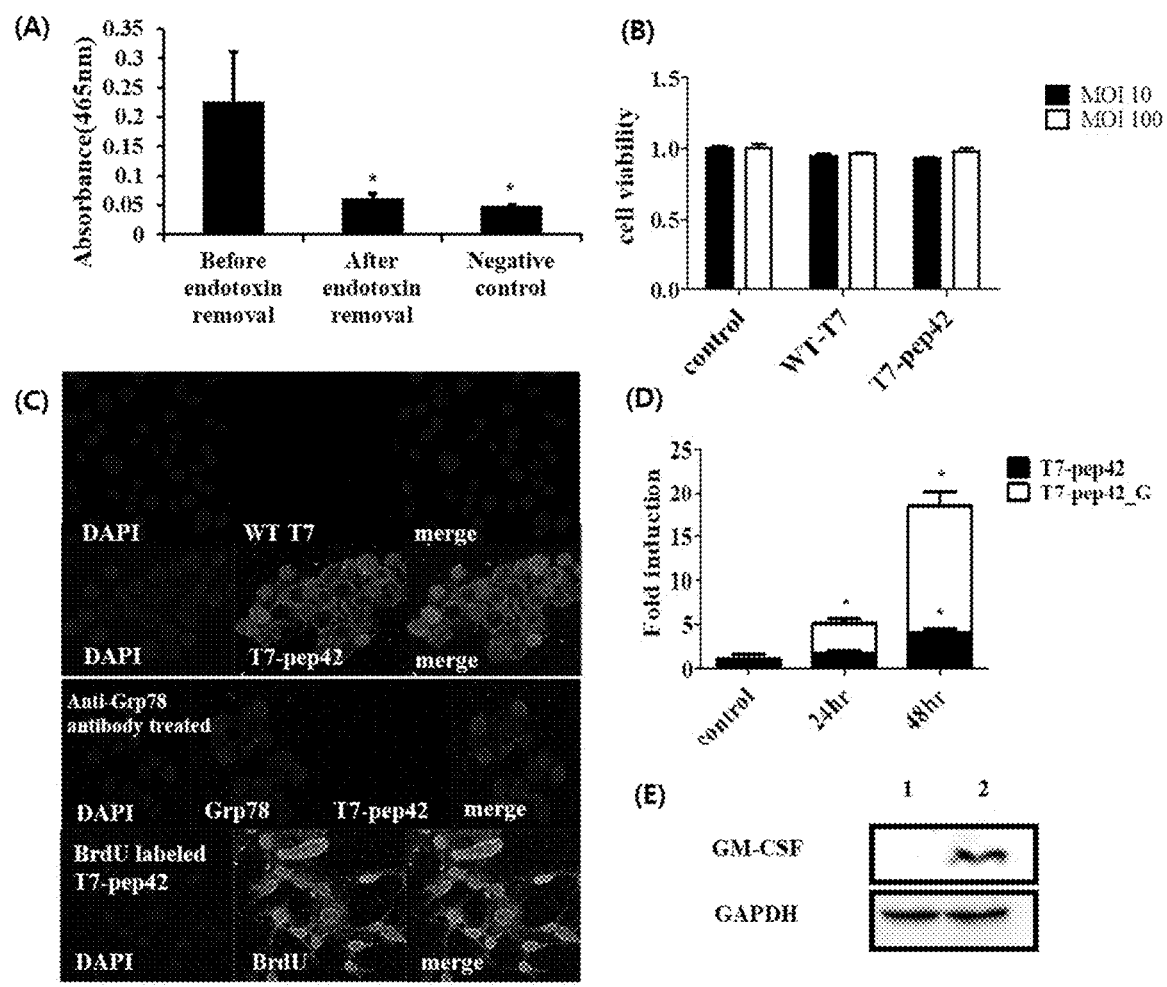
FIG. 2 is a result showing that the present bacteriophage binds to target cancer cells and the expression of GM-CSF is induced. A, removal of endotoxin after phage preparation. B, cell viability assay of B16F10 cells after exposure to bacteriophages. Two different concentrations (multiplicity of infection of either 10 or 100) of native T7 or engineered T7 were added to the culture and incubated for 24 hours before MTT assay was performed. C, homing and internalization of phage particle, and nuclear localization of phage DNA. First and second row: wild type phage T7 (WT T7) or T7 displaying the homing peptide (T7-pep42) was added to in vitro cultured B16F10 melanoma cells and binding was observed under a fluorescent laser scanning confocal microscope. The nucleus was stained with DAPI (blue) and the phage particle was stained with anti-T7 antibody (green). Third row: B16F10 cells were first treated with anti-Grp78 antibody (red) to mask the receptor for pep42. Then T7-pep42 (green) was added and binding was observed. Fourth row: T7-pep42 was produced in the presence of BrdU (green) to label the genomic DNA and added to cultured B16F10 cells. Internalized phage DNA to DAPI (blue) stained nucleus is shown. D, realtime RT-PCR analysis of mRNA encoding GM-CSF from T7-pep42 or T7-pep42_G transduced B16F10 cells. Relative amounts of mRNA encoding GM-CSF from cells treated with T7-pep42 or T7-pep42_G are shown in black or white bars, respectively. T7-pep42, phage T7 displaying pep42; T7-pep42_G, phage T7 displaying pep42 and expressing GM-CSF. E, western blot analysis of GM-CSF from T7-pep42 transduced B16F10 cells (lane 2) and empty cell (lane 1). GAPDH was used as an internal control. For statistical analysis, one way ANOVA was performed and then Tukey's test was conducted. * or ** above each vertical bar indicates statistical significance of each test to the control. * or ** above each horizontal bar indicates statistical significance of each test between corresponding pairs.

For this, an MTT assay was performed with the results indicating that neither wild type T7, nor its engineered version, had a significant effect on the viability of murine melanoma cells (FIG. 2, A).

Next, it was tested whether the present engineered phage homes into B16F10 cells in vitro. Both wild type T7 and its engineered version were added to the cultures of murine melanoma cells and stained with anti-T7 antibody followed by observation under laser scanning confocal fluorescent microscope (FIG. 2, B). As a result, it was found that wild type T7 was all washed out while the engineered T7 displaying pep42 remained attached to the cytoplasm and even to the nucleus of melanoma cells. It was observed that the phage particles were localized in the nuclei, indicating the expression of GM-CSF from the cassette inserted into the phage genome DNA in the transduced culture of melanoma cells. The transcription from the GM-CSF cassette was confirmed by real time RT-PCR in a time-dependent manner (FIG. 2, C). The expression of GM-CSF was also observed by western blot (FIG. 2, D).

Figure 3:
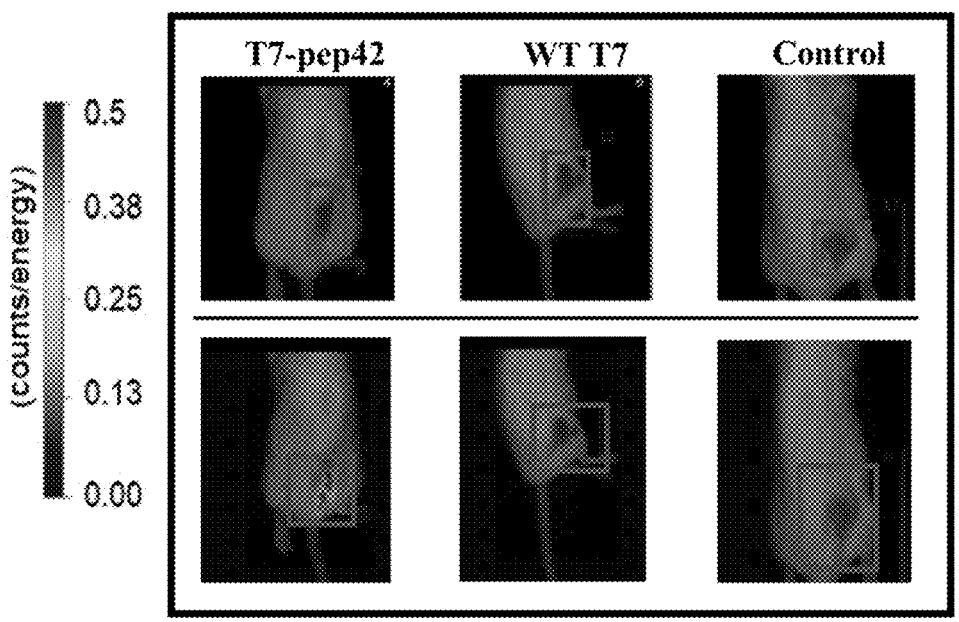
FIG. 3 is a result showing in vivo imaging of the mouse treated with the present phage. For this, mice were injected with B16F10 cells to develop tumor and the present engineered phage or the regular not-engineered phages were intravenously injected into the mice and the in vivo imaging of the mice was performed.
Figure 3:
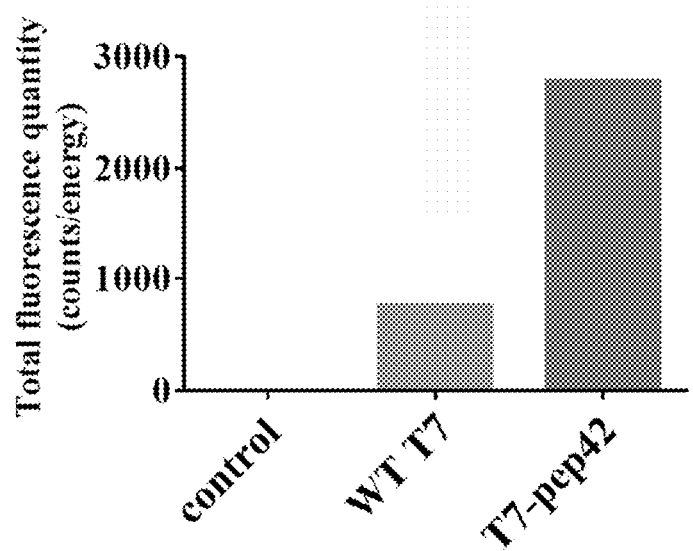

As the present phage engineered to homing to the target cells was confirmed to bind to the cells in vitro, the homing activity of the phage was then tested in vivo. For this, B16F10 cells were grafted into the mice, and allowed to grow as tumor masses. Then, either wild type phage T7, or the present engineered phage was injected intravenously into the mice and in vivo live imaging was performed (FIG. 3). Fluorescently labeled phage T7 displaying pep42 was found be localized to the tumor masses four times more than wild type T7. The wild type T7 was found to be peritumorally localized, rather than intratumorally, while the majority of the engineered T7 was localized intratumorally.

Example 3. Inhibition of Tumor Growth by the Present Bacteriophage T7

Figure 4:
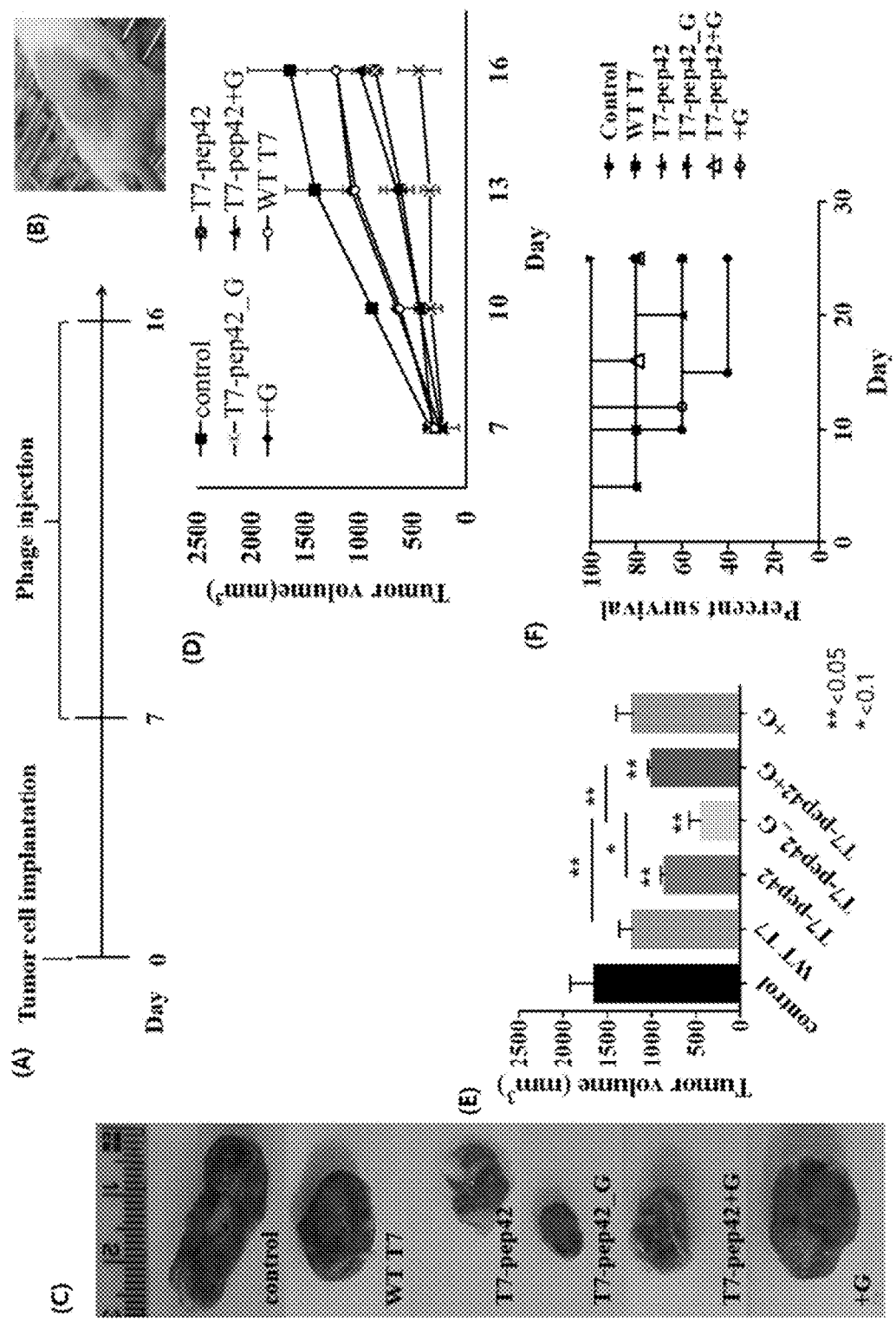
FIG. 4 shows a treatment plan and therapeutic effects of the present bacteriophage on B16F10. A: Treatment plan in which B16F10 mouse melanoma cells were grafted into the mouse and the cells were allowed to grow for 1 week. After that the present bacteriophages were intravenously injected into the mouse once a day for 10 days. B: The right flank of the mouse grafted with the tumor cells. C: A graph showing the changes in tumor size measured at 7, 10, 13 and 16 days after the treatment. D: A graph showing the size of tumors at the last day of the measurement. E: Tumor samples removed from the mouse at the last day of the measurement. F: Survival rates of the mice observed for 25 days.
Figure 5:
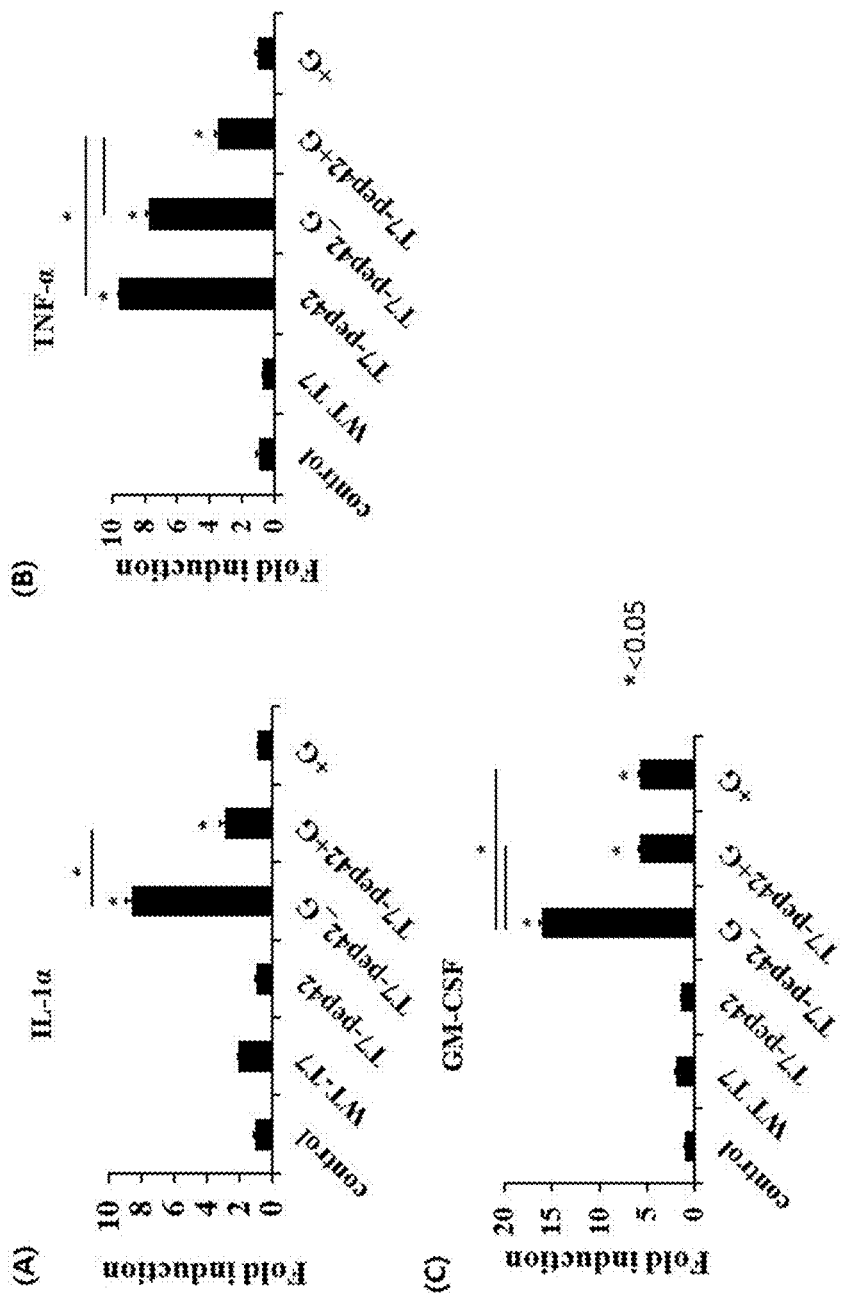
FIG. 5 is a result showing the increased level of inflammatory cytokines in serum by the present bacteriophage. Mice were sacrificed after 10 daily treatments of each phage and/or GM-CSF, and serum cytokine was measured using cytokine ELISA. A, IL1α. B; TNF-α; C, GM-CSF. WT T7, wild type phage T7; T7-pep42, phage T7 displaying pep42; T7-pep42_G, phage T7 displaying pep42 and expressing GM-CSF; T7-pep42+G, phage T7 displaying pep42 and externally added protein cytokine GM-CSF; +G, externally added protein cytokine GM-CSF. For statistical analysis, one way ANOVA was performed and Tukey's test was conducted. * or ** above each vertical bar indicates statistical significance of each test to the control. * or ** above each horizontal bar indicates statistical significance of each test between corresponding pairs.

It was confirmed that the present engineered bacteriophage T7 was intratumorally localized in vivo and the GM-CSF was expressed from the transduced phage in vitro. Next the tumor inhibitory activity of the present bacteriophage in vivo was tested. For this, B16F10 mouse melanoma cells cultured in vitro were grafted into the mouse and allowed to grow for 7 days before the treatment with the present bacteriophage started. The present bacteriophage was intravenously injected once every day for 10 days and the survival, and changes in tumor masses were observed (FIGS. 4, A and B). Tumor mass was measured at 7, 10, 13, and 16 days post grafting with various treatments (FIGS. 4. C and D). As a result, it was found that wild type T7 inhibited the tumor growth by 29%. In contrast, the present phage displaying homing peptide (pep42) inhibited the tumor growth by 51% and the phage T7 displaying homing peptide and expressing GM-CSF (T7-pep42_G) inhibited tumor growth by 72%. The addition of GM-CSF as cytokines had an effect in the inhibition of tumor growth similar to that of wild type T7. At a given concentration, the combination of T7 displaying pep42 and the GM-CSF intravenously administered did not produce additive effect. The amount of GM-CSF available in vivo may be one of the key factors in the present method (FIG. 5). Or, the availability of GM-CSF in tumor micro environment may be another determinant. The mice treated with the phage expressing GM-CSF were all alive at the end of the experiment (FIG. 4, F). 60% of the mice treated with phage display homing peptide or with protein GM-CSF were survived, and early death was observed in the mice treated with wild type phage.

Animal cells are not natural host for bacteriophages, and therefore the cells lysis cannot be expected from the phage infection and multiplication. One possibility for the lysis of tumor cells is immunological attack. Since the recruitment of immune cells to the tumor could be mediated by various cytokines, the increased level of serum cytokines after the treatment by the present phage were analyzed (FIG. 5). The serum levels of three inflammatory cytokines IL-1α, TNF-α, and GM-CSF were measured. As results, 8- or 3-fold increases in serum IL-1α level were observed when the mice were administered with phage T7 displaying pep42 and expressing GM-CSF (T7-pep42_G) or phage T7 displaying pep42 plus the externally added protein GM-CSF (T7-pep42+G), respectively. Treatment with phage alone or protein GM-CSF alone did not lead to any increase (FIG. 5, A). In contrast, Homing phage displaying pep42 increased serum level of TNF-α (FIG. 5, B). In case of GM-CSF, the pattern of increase was similar to the pattern of IL-1α except the presence of exogenously expressed or added GM-CSF (FIG. 5, C).

Figure 6:
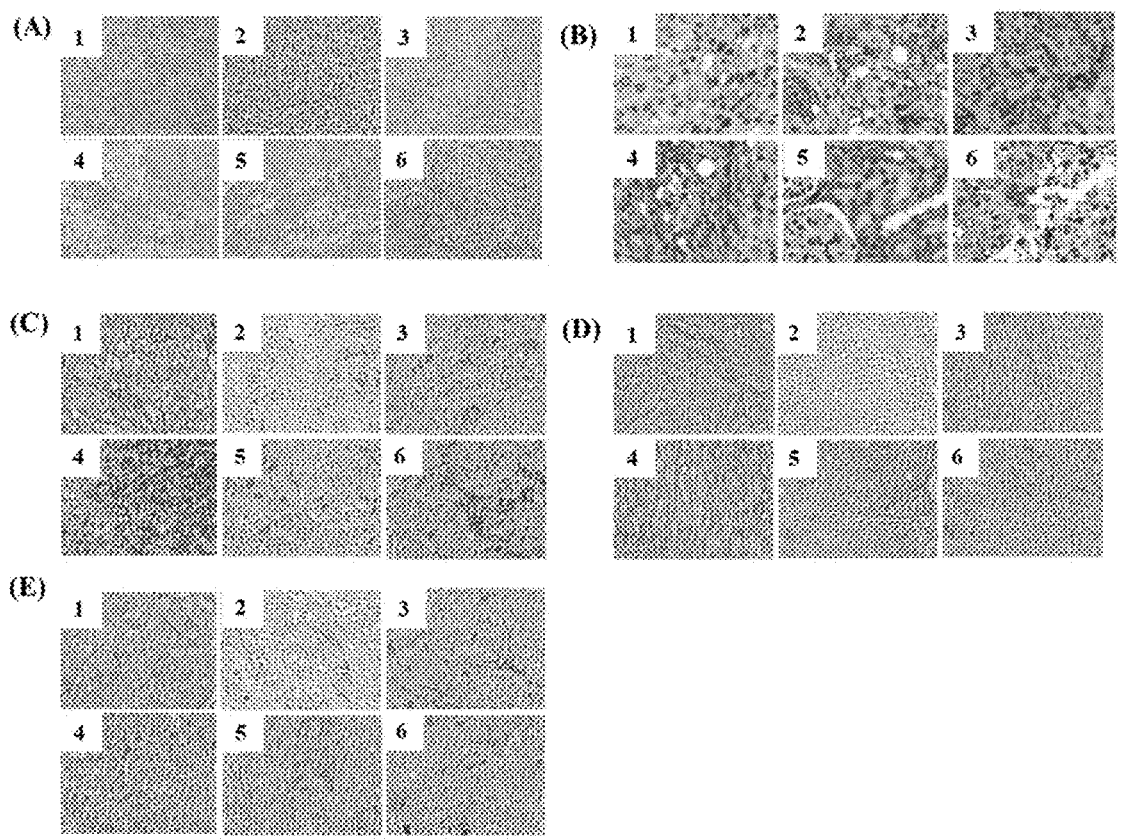
FIG. 6 is a result showing that the expression of cytokines as in FIG. 5 can recruit various immune cells. A: H&E staining showing the changes in tumor size and damaged cells before and after the treatment with the present engineered bacteriophage. B: Immunohistostaining result of CD8+ T cells. C: Immunohistostaining result of CD11+ dendritic cells. D: Immunohistostaining result of CD49+NK cells. E: Immunohistostaining result of macrophages. Each lane indicates: 1, control; 2, WT-T7; 3, T7-pep42; 4, T7-pep42_G; 5, +G; 6, T7-pep42+G.

As the expression of cytokines could lead to the activation and recruitment of immune cells to tumor mass, mice bearing tumor mass were treated with phages and/or cytokine GM-CSF, and immunohistochemical observation was performed (FIG. 6). After the treatment with the recombinant phage, massive necrotic or damaged tumor cells were seen after treatment with the recombinant phage (FIG. 6, A). Tumor destruction and the shrinkage of cells were most prominent in mice treated with phage T7 displaying pep42 and GM-CSF which was either expressed from the phage or externally added. Wild type T7, T7 displaying pep42, or externally added protein GM-CSF alone, induced a limited destruction of tumor mass and shrinkage of cells. The highest degree of macrophage infiltration was observed when both T7 displaying pep42 and GM-CSF were present (FIG. 6, B). Lesser infiltration was seen in the group treated with T7 displaying pep42 or GM-CSF alone. Wild-type T7 even induced a limited macrophage infiltration. For dendritic cell (DC) or cytotoxic T cells, T7 displaying pep42 and expressing GM-CSF showed highest degree of infiltration, the groups treated with T7 displaying pep42 alone, T7 displaying pep42 with added GM-CSF and GM-CSF alone showed infiltration to a lesser extent (FIGS. 6, C and D). Considering the amount of total GM-CSF detected in FIG. 5, C, GM-CSF played an important role in recruiting the immune cells. Even wild type T7 induced a limited degree of immune cell infiltration. For NK cells, T7 displaying pep42 and expressing GM-CSF induced the same degree of immune cell infiltration (FIG. 6, E). Wild type T7 appeared to play little role in NK cell infiltration.

Figure 7:
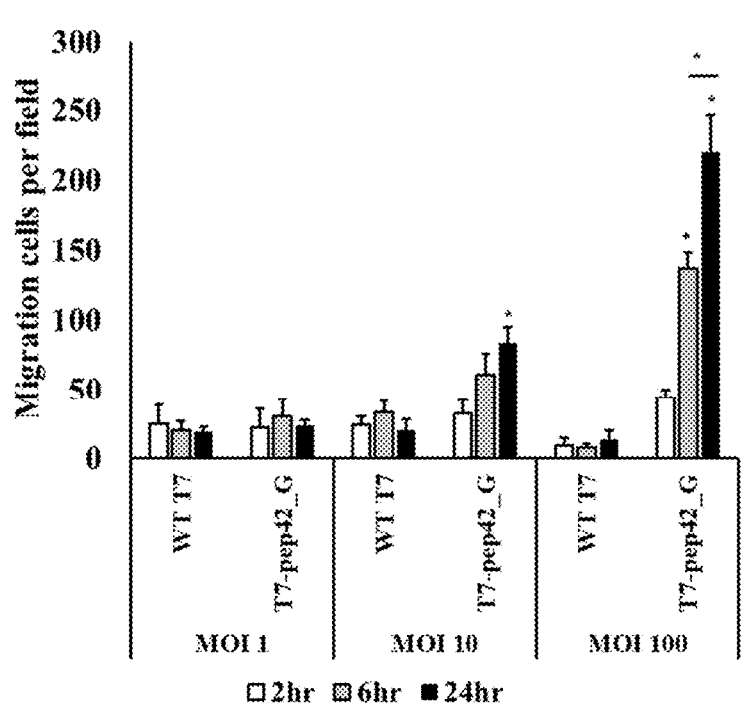
FIG. 7 is a result of the analysis in which T7 bacteriophage displaying various concentrations of Pep42 and expressing GM-CSF, or non-engineered T7 as control was added and the migration of macrophages were observed at various time points. Cultured B16F10 cells in the lower chamber were treated with 3 different titers (MOI 1, 10, or 100) of wild type T7 (WT T7) or T7 displaying the homing peptide and harboring an mammalian expression cassette of GM-CSF (T7-pep42_G). Macrophages (RAW264.7) in the upper chamber were allowed to migrate for 3 different time periods. A, staining and visualization of membrane after migration. White pores are seen from the membrane and macrophages are stained with crystal violet. B, 3 random fields were chosen and the migrated cells were quantitated. For statistical analysis Tukey's test was performed. * or ** above each vertical bar indicates statistical significance of each test to the control. * or ** above each horizontal bar indicates statistical significance of each test between corresponding pairs.

For quantitative analysis of phage-induced macrophage infiltration quantitatively in vitro, transwell migration assay was performed. Various doses of either wild type T7 or T7 displaying pep42 and expressing GM-CSF (T7-pep42_G) were added and macrophage migration was detected at various time points (FIG. 7). Wild type T7 did not induced the migration of macrophage, while T7 expressing GM-CSF induced a massive recruitment of macrophages in both dose- and time-dependent manners.

The above results indicate that the phage constructed in the present disclosure was successfully transduced to B16F10 melanoma cells in vitro and in vivo, and GM-CSF was expressed from the transduced phage DNA. Also, the mice treated with the present phage by intravenous injection all survived until the end of the experiment for 25 days. In contrast, only 40% of untreated mice survived. Furthermore, the tumor size of mice not treated with phage for 10 days increased by 400%, whereas the tumor size of mice treated with phage constructed according to the present invention was only 12% larger. In addition, serum cytokine concentrations such as IL-1α, TNF-α and GM-CSF have also been shown to increase during the treatment. Immunohistochemical analysis of tumor tissues also showed infiltration of macrophages, dendritic cells, CD8 positive T cells and natural killer cells (Natural Killer). Migration of mouse macrophages and T cells was also shown in in vitro transwell migration assays. Taken together, the results indicate that the recombinant T7 bacteriophage according to the present disclosure can inhibit tumor growth by altering the microenvironment of the tumor and recruiting anti-tumor immune cells.

The various singular/plural permutations may be expressly set forth herein for sake of clarity. Although a few embodiments of the present disclosure have been shown and described, it would be appreciated by those skilled in the art that changes may be made in this embodiment without departing from the principles and sprit of the invention, the scope of which is defined in the claims and their equivalents.

Unless defined or interpreted otherwise, all technical and scientific terms and any acronyms used herein have the same meanings as commonly understood by one of ordinary skill in the art in the field of the invention. The contents of all publications disclosed as references herein are incorporated herein by reference.

What is claimed is:

1. An oncolytic recombinant bacteriophage T7 displaying on its capsid a tumor specific homing peptide and comprising a cytokine gene in the genome for expression in a mammalian eukaryotic cell,
   wherein:
   the cytokine is GM-CSF (Granulocyte-Macrophage Colony-Stimulating Factor),
   the cytokine gene is integrated into a Pac I restriction site located at 27223 bp-27230 bp of the T7 genome based on the sequence set forth in SEQ ID NO: 10, and
   the tumor specific homing peptide is represented by the amino acid sequence of CTVALPGGYVRVC set forth in SEQ ID NO: 1 for melanoma.

2. A composition comprising the recombinant bacteriophage T7 of claim 1.

3. The composition of claim 2, wherein the composition is for treating melanoma.

* * * * *